(12) United States Patent
Craig et al.

(10) Patent No.: US 6,949,669 B2
(45) Date of Patent: Sep. 27, 2005

(54) ORGANIC COMPOUNDS

(75) Inventors: Gerald Wayne Craig, Basel (CH); Martin Eberle, Bottmingen (CH); Martin Zeller, Baden (CH); Steven Scott Bondy, San Diego, CA (US); Daniel Dennis Comer, San Diego, CA (US); Soan Cheng, San Diego, CA (US); Julie Elizabeth Penzotti, San Diego, CA (US); Peter Grootenhuis, San Diego, CA (US); Jürg Ehrler, Sursee (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 57 days.

(21) Appl. No.: 10/181,878

(22) PCT Filed: Jan. 23, 2001

(86) PCT No.: PCT/EP01/00718

§ 371 (c)(1),
(2), (4) Date: Oct. 18, 2002

(87) PCT Pub. No.: WO01/55066

PCT Pub. Date: Aug. 2, 2001

(65) Prior Publication Data

US 2004/0049065 A1 Mar. 11, 2004

(30) Foreign Application Priority Data

Jan. 25, 2000 (GB) ............................................. 0001702
Aug. 22, 2000 (GB) ............................................. 0020686

(51) Int. Cl.$^7$ .................... C07C 255/01; C07C 255/45; C07C 255/49; A01N 37/34

(52) U.S. Cl. ...................... 558/410; 514/520; 504/309; 504/310

(58) Field of Search ......................... 558/410; 514/520; 504/309, 310

(56) References Cited

FOREIGN PATENT DOCUMENTS

WO       WO99/07674       * 2/1999

OTHER PUBLICATIONS

Chowdhury et al. Journal of Organic Chemistry, (1998), vol. 63, pp. 1863–1871.*

* cited by examiner

*Primary Examiner*—Joseph K. McKane
*Assistant Examiner*—Rebecca Anderson
(74) *Attorney, Agent, or Firm*—Thomas Hamilton

(57) ABSTRACT

Compounds of general formula (I) wherein the substituents are as defined in claim 1 are suitable for use as herbicides

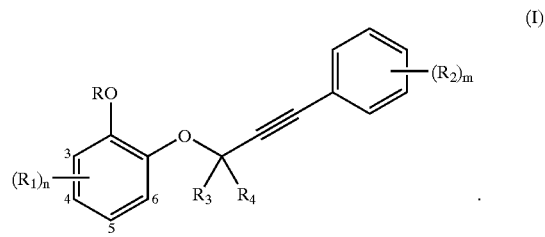

11 Claims, No Drawings

ORGANIC COMPOUNDS

This Appilcation is a 371 of PCT/EP01/00718 filed Jan. 2001.

The present invention relates to novel herbicidally active organic compounds (substituted 3-phenoxy-1-phenyl acetylene derivatives), to their preparation, to compositions comprising said compounds, and to the use thereof for controlling weeds, in particular in crops of cultivated plants or for inhibiting plant growth.

Herbicidally active 4-(alkoxycarbonylamino)-phenol derivatives are disclosed, for example, in Derwent 1999-379868/32 (JP-A 11147866).

Novel substituted 3-phenoxy-1-phenyl acetylene derivatives having herbicidal and growth-inhibiting properties have now been found.

Accordingly, the invention relates to compounds of the general formula I

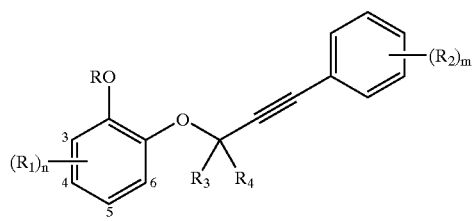

wherein

R is H, —$COR_{12}$, —$S(O)_qC_{1-8}$alkyl, $C_{1-8}$alkyl optionally substituted by one or more substituents selected from halogen, $C_{1-4}$alkoxy, —CN, —$S(O)_qC_{1-8}$alkyl and phenyl optionally substituted by one or more substituents selected from halogen, $C_{1-4}$alkyl, halo-$C_{1-4}$alkyl, $C_{1-4}$alkoxy, —CN, —$NO_2$ and —$S(O)_qC_{1-8}$alkyl, $C_{3-8}$alkenyl optionally substituted by one or more substituents selected from halogen, $C_{1-4}$alkoxy, cyano and phenyl optionally substituted by one or more substituents selected from halogen, $C_{1-4}$alkyl, halo-$C_{1-4}$alkyl, $C_{1-4}$alkoxy,, —CN, —$NO_2$ and —$S(O)_qC_{1-8}$alkyl, $C_{3-8}$alkinyl optionally substituted by one or more substituents selected from halogen, $C_{1-4}$alkoxy, cyano and phenyl optionally substituted by one or more substituents selected from halogen, $C_{1-4}$alkyl, halo-$C_{1-4}$alkyl, $C_{1-4}$alkoxy,, —CN, —$NO_2$ and —$S(O_2)C_{1-8}$alkyl $C_{3-6}$cycloalkyl optionally substituted by one or more substituents selected from halogen, $C_{1-4}$ alkoxy, cyano and phenyl optionally substituted by one or more substituents selected from halogen, $C_{1-4}$alkyl, halo-$C_{1-4}$alkyl, $C_{1-4}$alkoxy,, —CN, —$NO_2$ and —$S(O)_qC_{1-8}$alkyl, or phenyl optionally substituted by one or more substituents selected from halogen, —$CH_3$, —$CF_3$, —$OCH_3$, —CN, —$NO_2$ and —$S(O)_qC_{1-8}$alkyl; and if n is a number 0, 1, 2 or 3, R is also $C_{1-6}$alkylene, optionally interrupted by one oxygen and excluding an oxygen-oxygen-bond, forming a 5- to 9-membered ring fused to the benzene and optionally substituted by $C_{1-6}$alkyl or is $C_{2-6}$alkenylene, optionally interrupted by one oxygen and excluding an oxygen-oxygen-bond, forming a 5- to 9-membered ring fused to the benzene and optionally substituted by $C_{1-6}$alkyl, whereby said alkylene or alkenylene is bonded to the 3-position of the benzene;

$R_1$ is halogen, —CN, —SCN, —$SF_5$, —$NO_2$, —$NR_5R_6$, —$CO_2R_7$, —$CONR_8R_8R_9$, —$C(R_{10})$=$NOR_{11}$, —$COR_{12}$, —$XR_{13}$, $C_{1-8}$-alkyl optionally substituted by one or more substituents selected from halogen, —CN, —$NO_2$, —$NR_5R_6$, —$CO_2R_7$, —$CONR_8R_9$, —$COR_{12}$, —$C(R_{10})$=$NOR_{11}$, —$CSNR_8R_9$, —$C(S$—$C_{1-4}$alkyl)=$NR_8$, —$XR_{13}$, and $C_{3-6}$cycloalkyl, $C_{2-8}$alkenyl optionally substituted by one or more substituents selected from halogen, —CN, —$NO_2$, —$CO_2R_7$, —$CONR8R_9$, —$COR_{12}$, —$C(R_{10})$=$NOR_{11}$, —$CSNR_8R_9$, —$C(S$—$C_{1-4}$alkyl)=$NR_8$ and $C_{3-6}$cycloalkyl or $C_{2-8}$alkinyl optionally substituted by or more substituents selected from halogen, —CN, —$CO_2R_7$, —$CONR_8R_9$, —$COR_{12}$, —$C(R_{10})$=$NOR_{11}$, —$CSNR_8R_9$, —$C(S$—$C_{1-4}$alkyl)=$NR_8$ and $C_{3-6}$cycloalkyl, $C_{3-6}$cycloalkyl optionally substituted by one or more substituents selected from halogen, —CN, —$CO_2R_7$, —$CONR_8R_9$, —$COR_{12}$, —$C(R_{10})$=$NOR_{11}$, —$CSNR_8R_9$ and —$C(S$—$C_{1-4}$alkyl)=$NR_8$ or phenyl optionally substituted by one or more substituents selected from halogen, $C_{1-4}$alkyl, halo-$C_{1-4}$alkyl, $C_{1-4}$alkoxy,, —CN, —$NO_2$ and —$S(O)_qC_{1-8}$alkyl; and two adjacent $R_1$ are also $C_{1-7}$alkylene, optionally interrupted by 1 or 2 oxygens and excluding an oxygen-oxygen-bond, forming a 5- to 9-membered ring fused to the benzene and optionally substituted by $C_{1-6}$alkyl or is $C_{2-7}$alkenylene, optionally interrupted by 1 or 2 oxygens and excluding an oxygen-oxygen-bond, forming a 5- to 9-membered ring fused to the benzene and optionally substituted by $C_{1-6}$alkyl;

$R_2$ is halogen, —CN, —SCN, —$SF_5$, —$NO_2$, —$NR_5R_6$, —$CO_2R_7$, —$CONR_8R_9$, —$C(R_{10})$=$NOR_{11}$, —$COR_{12}$, —$XR_{13}$, —$OR_{16}$, —$N([CO]_pR_{17})COR_{17}$, —$N(OR_{17})COR_{17}$, —$N(R_{17})CO_2R_{17}$, —N—phthalimid, $C_{1-8}$-alkyl optionally substituted by one or more substituents selected from halogen, —CN, —$NO_2$, —$NR_5R_6$, —$CO_2R_7$, —$CONR_8R_9$, —$COR_{12}$, —$C(R_{10})$=$NOR_{11}$, —$CSNR_8R_9$, —$C(S$—$C_{1-4}$alkyl)=$NR_8$, —$XR_{13}$, —$N(R_{14})CO_2R_{15}$, —$N(R_{14})COR_{15}$ and $C_{3-6}$cycloalkyl, $C_{2-8}$alkenyl optionally substituted by one or more substituents selected from halogen, —CN, —$NO_2$, —$CO_2R_7$, —$CONR_8R_9$, —$COR_{12}$, —$C(R_{10})$=$NOR_{11}$, —$CSNR_8R_9$, —$C(S$—$C_{1-4}$alkyl)=$NR_8$ and $C_{3-6}$cycloalkyl, $C_{2-8}$alkinyl optionally substituted by one or more substituents selected from halogen, —CN, —$CO_2R_7$, —$CONR_8R_9$, —$COR_{12}$, —$C(R_{10})$=$NOR_{11}$, —$CSNR_8R_9$, —$C(S$—$C_{1-4}$alkyl)=$NR_8$ and $C_{3-8}$cycloalkyl, or $C_{3-6}$cycloalkyl optionally substituted by one or more substituents selected from halogen, —CN, —$CO_2R_7$, —$CONR_8R_9$, —$COR_{12}$, —$C(R_{10})$=$NOR_{11}$, —$CSNR_8R_9$ and —$C(S$—$C_{1-4}$alkyl)=$NR_8$; and two adjacent $R_2$ are also $C_{1-7}$alkylene, optionally interrupted by 1 or 2 oxygens and excluding an oxygen-oxygen-bond, forming a 5- to 9-membered ring fused to the benzene and optionally substituted by $C_{1-6}$alkyl or is $C_{2-7}$alkenylene, optionally interrupted by 1 or 2 oxygens and excluding an oxygen-oxygen-bond, forming a 5- to 9-membered ring fused to the benzene and optionally substituted by $C_{1-6}$alkyl;

$R_5$ is H or $C_{1-8}$alkyl;

$R_6$ is H, $C_{1-8}$alkyl, $C_{3-8}$alkenyl, $C_{3-8}$alkinyl, benzyl optionally substituted by one or more substituents selected from halogen, $C_{1-4}$alkyl, halo-$C_{1-4}$alkyl, $C_{1-4}$alkoxy, —CN, —$NO_2$ and —$S(O_2)C_{1-8}$alkyl or phenyl optionally substituted by one or more substituents selected from halogen, $C_{1-4}$alkyl, halo-$C_{1-4}$alkyl, $C_{1-4}$alkoxy, —CN, —$NO_2$ and —$S(O)_qC_{1-8}$alkyl; or $R_5$ and $R_6$ together are $C_{2-5}$alkylene;

$R_7$ is H, $C_{1-8}$alkyl optionally substituted by one or more substituents selected from halogen and $C_{1-4}$alkoxy, $C_{3-8}$alkenyl optionally substituted by one or more halogen, $C_{3-8}$alkinyl optionally substituted by one or more halogen or phenyl optionally substituted by one or more substituents selected from halogen, $C_{1-4}$alkyl, halo-$C_{1-4}$alkyl, $C_{1-4}$alkoxy, —CN, —NO$_2$ and —S(O)$_q$ $C_{1-8}$alkyl;

$R_8$ is H or $C_{1-8}$alkyl;

$R_9$ is H, $C_{1-8}$alkyl optionally substituted by one or more substituents selected from —CO$_2$R$_8$ and —CN, $C_{3-8}$alkenyl, $C_{3-8}$alkinyl, $C_{1-4}$alkoxy, benzyl optionally substituted by one or more substituents selected from halogen, $C_{1-4}$alkyl, halo-$C_{1-4}$alkyl, $C_{1-4}$alkoxy, —CN, —NO$_2$ and —S(O$_2$)$C_{1-8}$alkyl or phenyl optionally substituted by one or more substituents selected from halogen, $C_{1-4}$alkyl, halo-$C_{1-4}$alkyl, $C_{1-4}$alkoxy, —CN, —NO$_2$ and —S(O)$_q$$C_{1-8}$alkyl; or $R_8$ and $R_9$ together are $C_{2-5}$alkylene;

$R_{10}$ is H, $C_{1-4}$alkyl, halo-$C_{1-4}$alkyl or $C_{3-6}$cycloalkyl;

$R_{11}$ is H, $C_{1-8}$alkyl, $C_{3-8}$alkenyl, $C_{3-8}$alkinyl or halo-$C_{1-4}$ alkyl;

$R_{12}$ is H, $C_{1-4}$alkyl, halo-$C_{1-4}$alkyl or $C_{3-6}$cycloalkyl;

$R_{13}$ is $C_{1-8}$alkyl optionally substituted by one or more substituents selected from halogen, —CN and $C_{1-4}$alkoxy, $C_{3-8}$alkenyl, $C_{3-8}$alkinyl or, if X is —O— or —S—, also H;

$R_{14}$ is H or $C_{1-8}$alkyl or $C_{1-8}$alkoxy;

$R_{15}$ is H, $C_{1-8}$alkyl;

$R_{16}$ is $C_{0-6}$alkylphenyl optionally substituted by one or more substituents selected from halogen, $C_{1-4}$alkyl, halo-$C_{1-4}$alkyl, $C_{1-4}$alkoxy, —CN, —NO$_2$ and —S(O$_2$) $C_{1-8}$alkyl;

$R_{17}$ is H, $C_{1-8}$alkyl or phenyl optionally substituted by one or more substituents selected from halogen, $C_{1-4}$alkyl, halo-$C_{1-4}$alkyl, $C_{1-4}$alkoxy, —CN, —NO$_2$ and —S(O)$_q$ $C_{1-8}$alkyl;

X is —O—, —S—, —SO—, —S(O$_2$)— or —OS(O$_2$)—

$R_3$ or $R_4$ are independent of one another H, halogen, —CN, $C_{1-4}$alkyl or $C_{1-4}$alkoxy; or $R_3$ and $R_4$ together are $C_{2-5}$alkylene;

n is a number 0, 1, 2, 3 or 4;

m is a number 0, 1, 2, 3, 4 or 5; and the sum of n and m is equal or greater than 1;

p is a number 0 or 1; and q is a number 0, 1 or 2.

In case of the substitution of one of the aforementioned radicals by more than one substituent, these substituents may be independently selected and therefore may be the same or different. For example, $C_{1-8}$alkyl optionally substituted by one or more substituents selected from halogen, $C_{1-4}$alkoxy, cyano and phenyl may be: —CF$_3$, —CHClCH$_2$CH$_2$CF$_3$ or —CHClCH$_2$CH$_2$—O—C$_2$H$_5$.

Halogen is F, Cl, Br and J, whereby F, Cl and Br are preferred.

Halo-$C_{1-4}$alkyl is $C_{1-4}$alkyl substituted by one or more halogen, for example —CF$_3$ or —CHClCF$_3$.

Alkyl, on its own or as a constituent of another substituent, is to be understood as meaning straight-chain or branched-chain alkyl. Depending on the number of carbon atoms indicated, alkyl is, for example: methyl, ethyl or the isomers of propyl, butyl, pentyl and hexyl, for example isopropyl, isobutyl, tert-butyl, sec-butyl or isopentyl. Preferebly, alkyl is methyl, ethyl or the isomers of propyl and butyl.

Depending on the number of carbon atoms indicated, alkenyl is, for example, 1-propenyl, allyl, 1-butenyl, 2-butenyl or 3-butenyl.

Depending on the number of carbon atoms indicated, alkinyl is, for example, 1-propynyl or 1-butynyl.

Depending on the number of carbon atoms indicated, cycloalkyl is cyclopropyl, cyclobutyl, cyclopentyl or cyclohexyl, preferably cyclopropyl, cyclopentyl or cyclohexyl.

R, two adjacent $R_1$ and two adjacent $R_2$ defined as $C_{1-6}$alkylene (or in case of $R_1$ or $R_2$ $C_{1-7}$alkylene), optionally interrupted by one (or in case of $R_1$ or $R_2$ 1 or 2) oxygen and excluding an oxygen-oxygen-bond, forming a 5- to 9-membered ring fused to the benzene and optionally substituted by $C_{1-6}$alkyl or as $C_{2-6}$alkenylene (or in case of $R_1$ or $R_2$ $C_{2-7}$alkenylene), optionally interrupted by one (or in case of $R_1$ or $R_2$ 1 or 2) oxygen and excluding an oxygen-oxygen-bond, forming a 5- to 9-membered ring fused to the benzene and optionally substituted by $C_{1-6}$alkyl is, for example, —CH$_2$—CH$_2$—CH$_2$—, —CH$_2$—O—, —CH$_2$—O—CH$_2$——CH$_2$—O—CH$_2$—CH$_2$—, —CH$_2$—O—CH=CH— or —O—CH$_2$—O—. Such substitution leads for example, to the following sub-structures:

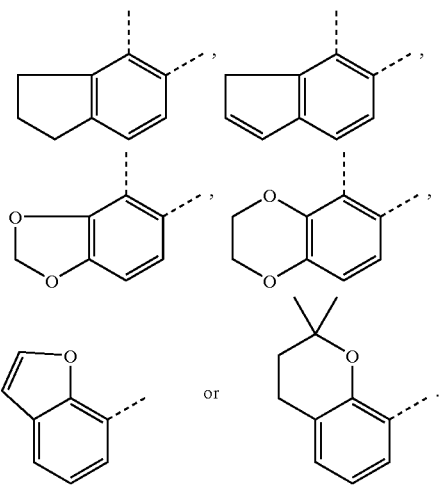

The invention is also directed to the enantiomers and salts of the compounds of formula I. Preferably, said salts are formed with amines, alkali metal bases and alkaline earth metal bases or quarternary ammonium bases. Salt-forming alkali metal and alkaline earth metal bases include the hydroxides of lithium, sodium, potassium, magnesium or calcium, those of sodium or potassium being especially preferred.

Illustrative examples of amines suitable for forming ammonium salts are ammonia, as well as primary, secondary, and tertiary $C_1$—$C_{18}$alkylamines, $C_1$—$C_4$hydroxyalkylamines and $C_2$–$C_4$alkoxyalkylamines, typically methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl ethylamine, methyl isopropylamine, methyl hexylamine, methyl nonylamine, methyl pentadecylamine, methyl octadecylamine, ethyl butylamine, ethyl heptylamine, ethyl octylamine, hexyl heptylamine, hexyl octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines such as pyridine, quinoline, isoquinoline, morpholine, piperidine, pyrrolidine, indoline, quinuclidine and azepine; primary arylamines such as anilines, methoxyanilines, ethoxyanilines, o-, m- and p-toluidines, phenylenediamines, benzidines, naphthylamines and o-, m- and p-chloroanilines. Preferred amines are triethylamine, isopropylamine and diisopropylamine.

Suitable quarternary ammonium bases for forming salts are, for example, $[N(R_aR_bR_cR_d)]^+ OH^-$, wherein $R_a$, $R_b$, $R_c$ and $R_d$ are independent $C_1$–$C_4$alkyl. Other suitable tetraalkyl ammonium bases with other anions may be obtained for example through anion exchange reactions.)

Preferred compounds of formula I are those wherein at least one substituent is or contains CN.

Also preferred compounds of formula I are those wherein R is H, $C_{1-8}$alkyl optionally substituted by one or more substituents selected from halogen and —CN.

Also preferred compounds of formula I are those wherein $R_1$ is halogen, —CN, —$NO_2$, —$C(R_{10})$=$NOR_{11}$, —$XR_{13}$, $C_{1-8}$-alkyl optionally substituted by one or more substituents —CN, or $C_{3-8}$alkenyl; $R_{10}$ is H or $C_{1-4}$alkyl; $R_{11}$ is $C_{1-8}$alkyl; and X is —O—, —$S(O_2)$— or —$OS(O_2)$—.

Also preferred compounds of formula I are those wherein $R_2$ is halogen, —CN, —$NO_2$, —$NR_5R_6$, —$CO_2R_7$, —$C(R_{10})$=$NOR_{11}$, —$XR_{13}$ or $C_{1-8}$-alkyl optionally substituted by one or more substituents selected from halogen, —CN and —$CO_2R_7$; $R_5$ is H; $R_6$ is H; $R_7$ is H or $C_{1-8}$alkyl; $R_{10}$ is H or $C_{1-4}$alkyl; $R_{11}$ is $C_{1-8}$alkyl and X is —O—, —$S(O_2)$— or —$OS(O_2)$—.

Also preferred compounds of formula I are those wherein $R_3$ or $R_4$ are independent of one another H or $C_{1-4}$alkyl.

Also preferred compounds of formula I are those wherein n is a number 0, 1 or 2; and m is a number 0, 1, 2, 3 or 4; and the sum of n and m is equal or greater 1.

Also preferred compounds of formula I are those wherein R is H, $C_{1-8}$alkyl optionally substituted by one or more substituents selected from halogen and —CN; $R_1$ is halogen, —CN, —$NO_2$, —$C(R_{10})$=$NOR_{11}$, —$XR_{13}$, $C_{1-8}$-alkyl optionally substituted by one or more substituents —CN; or $C_{3-8}$alkenyl; $R_2$ is halogen, —CN, —$NO_2$, —$NR_5R_6$, —$CO_2R_7$, —$C(R_{10})$=$NOR_{11}$,—$XR_{13}$ or $C_{1-8}$-alkyl optionally substituted by one or more substituents selected from halogen, —CN and —$CO_2R_7$; $R_5$ is H; $R_6$ is H; $R_7$ is H or $C_{1-8}$alkyl; $R_{10}$ is H or $C_{1-4}$alkyl; $R_{11}$ is $C_{1-8}$alkyl; $R_3$ or $R_4$ are independent of one another H or $C_{1-4}$alkyl; X is —O—, —$S(O_2)$— or —$OS(O_2)$—; n is a number 0, 1 or 2; and m is a number 0, 1, 2, 3 or 4; and the sum of n and m is equal or greater 1.

The compounds of formula I can be prepared by per se known processes as set forth in the following General Methods. In the following schemes the indication of one substituent $R_1$ or $R_2$ do not imply a limitation and it is understood that the substuents $R_1$ or $R_2$ may already be present in the starting compounds or introduced or further modified at a later reaction stage according to per se known general processes.

GENERAL METHODS

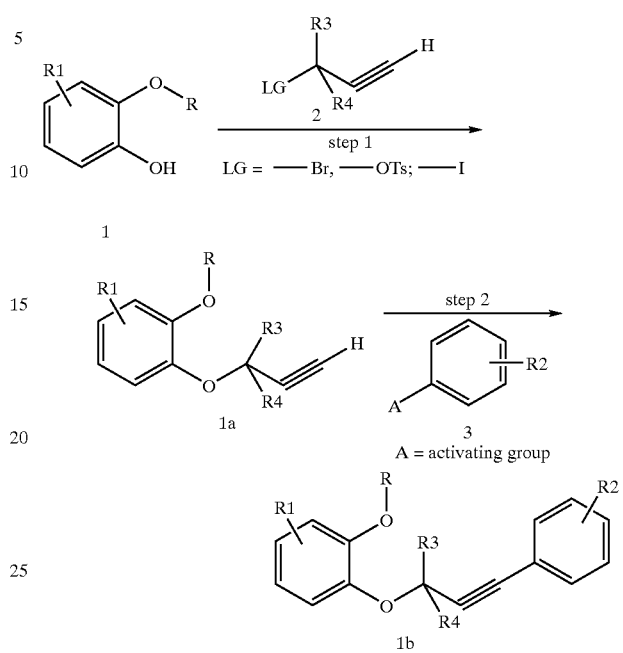

The preparation of the compounds 1b can be obtained by the following methods: Method A) Substituted phenols can be alkylated by the treatment with a base and propargylic derivatives, 2 under the conditions used for etherification of phenols, step 1. The propargylic ether is then coupled with an activated benzene using typical conditions for the Sonogashira reaction (K. Sonogashira, Comprehensive Organic Synthesis, vol 3, p-521, 1991) exemplified by the use of tetrakis triphenylphosphine palladium (II) and copper (I) iodide as the catalyst mixture. Activation of the benzene 3 usually requires that A is a leaving group such as iodide, bromide, tin group, borate group (J. Tsuji, Palladium Reagents and Catalysts—Innovations in Organic Synthesis, Chichester 1995), a trifluoromethanesulfonate (i.e. triflate, K. Ritter, Synthesis 735, 1993) or a hypervalent iodonium salt (R. M. Moriarty, Synthesis 431, 1990). There are special cases in which highly activated transition metals will also couple benzenes containing a chloride group (S. L. Buchwald, Angew. Chem. Int. Ed., 38, 2413, 1999). In cases where R is a suitable phenol protecing group (e.g. trimethylsilyl ether, methoxymethyl ether etc., T. W: Green, Protecting Groups in Organic Synthesis, John Wiley & Sons 1981), this group can be optionally removed by appropriate means and the subsequently deprotected hydroxyl group can be manipulated by methods described previously for Scheme 1, step 1.

Scheme 2

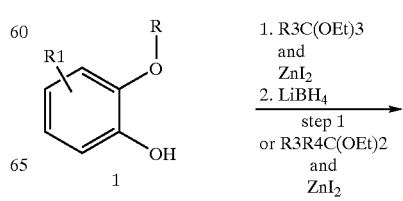

1. R3C(OEt)3 and ZnI2
2. LiBH4 step 1 or R3R4C(OEt)2 and ZnI2

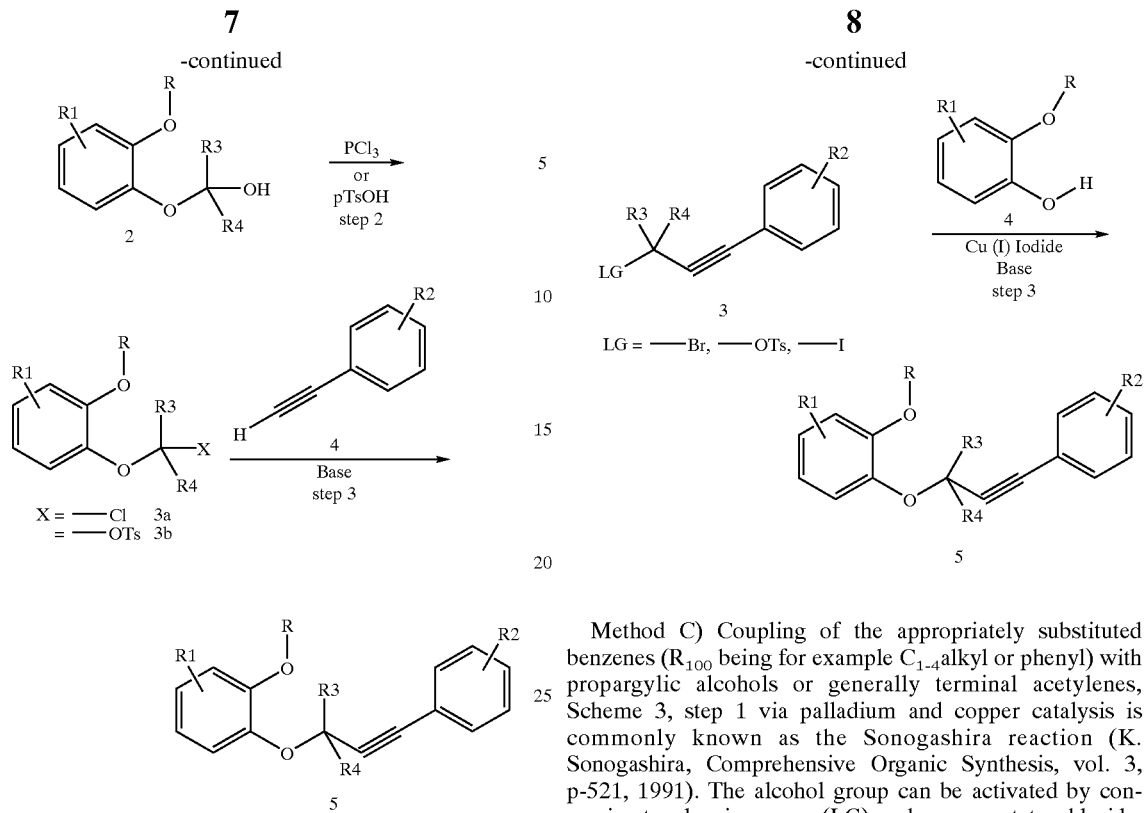

Method B) Reaction of a phenol with orthoformate esters followed by reduction, Scheme 2 step 1. This is equivalent to formation of the hemiketal, 2 reacting a phenol with a ketone (or aldehyde) or transketalization with an appropriate ketal partner (F. J. J. Meskens Synthesis 501, 1981). Treatment of this hemiacetal with halogenating or sulfonating reagents give the reactive hemichloro ether, 3a or hemisulfonate ether 3b respectively which can be directly displaced with acetylenes under strong basic conditions (e.g. lithium diisopropylamide, potassium hydride etc.).

Method C) Coupling of the appropriately substituted benzenes ($R_{100}$ being for example $C_{1-4}$alkyl or phenyl) with propargylic alcohols or generally terminal acetylenes, Scheme 3, step 1 via palladium and copper catalysis is commonly known as the Sonogashira reaction (K. Sonogashira, Comprehensive Organic Synthesis, vol. 3, p-521, 1991). The alcohol group can be activated by conversion to a leaving group (LG) such as an acetate, chloride, bromide, or a sulfonate ester which then facilitates subsequent displacement with substituted phenols, Scheme 3 step 3 (I. S. Mann, Synthesis 707, 1995).

Scheme 3

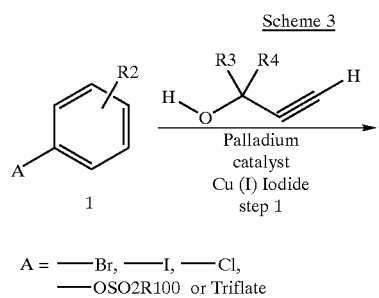

Scheme 4

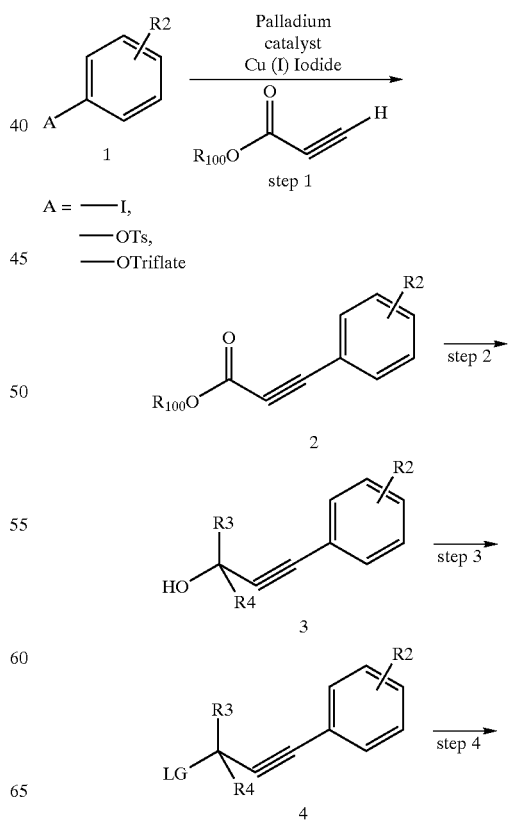

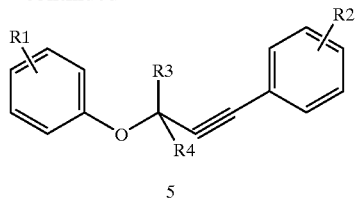

5

Method D) Phenyl acetylenic esters, 2 ($R_{100}$ being for example $C_{1-4}$alkyl or phenyl) can be prepared by the Sonogashira coupling of propargylic esters with activated benzenes, Scheme 4, step 1. These esters 2 can be either reduced or treated with metallated alkyls to give the corresponding alcohol which can then be further transformed into a leaving group (where LG is a bromide, methanesulfonate etc.) Scheme 3 step 2 for displacement with phenols to obtain the end product 5.

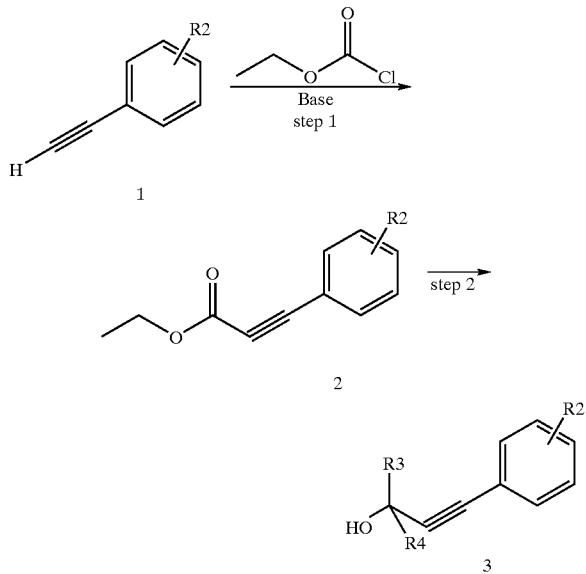

Method E) In Scheme 5 is a variant of the phenyl acetylenic ester strategy described in Scheme 4. This involves the direct treatment of a phenyl acetylene, 2 with methyllithium followed by quench with ethyl chloroformate to give the phenyl acetylenic ester (R. Rossi et. al Tet. Let 33, 4495, 1992). Subsequent reduction or Grignard addition step forms the phenyl propargylic alcohol, 3. Further elaboration to the end product, step 2 is the same as described in Scheme 4, step 3.

The reactions for obtaining the compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers, including diethyl ether, 1,2-dimethoxyethane, diglyme, tetrahydrofuran or dioxane, nitrites such as acetonitrile or propionitrile, amides such as N,N-dimethyl formamide, diethyl formamide or N-methylpyrrolidinone. The reaction temperatures are preferably in the range from −20° to +120° C. The reactions are usually slightly exothermic and can as a rule be carried out at room temperature. The reaction mixture can be heated for a brief time to boiling point to shorten the reaction time or also to initiate the reaction. The reaction times can also be shortened by addition of a few drops of a base as reaction catalyst. Particularly suitable bases are tertiary amines such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. Further suitable bases are also inorganic bases, typically hydrides such as sodium or calcium hydride, hydroxides such as sodium and potassium hydroxide, carbonates such as sodium and potassium carbonate, or hydrogencarbonates such as potassium and sodium hydrogencarbonate. The compounds of formula I can be isolated in conventional manner by concentrating the reaction mixture and/or removing the solvent by evaporation and by recrystallising or triturating the solid residue in a solvent in which it is not readily soluble, typically an ether, an aromatic hydrocarbon or a chlorinated hydrocarbon.

The compounds of formula I or compositions containing them may be used according to this invention by all standard methods of application used in agriculture, including preemergence application, postemergence application and seed dressing, as well as by different methods and techniques such as controlled release. For controlled release, a solution of the herbicide is applied to a mineral granular carrier or to a polymerised granulate (urea/formaldehyde) and then dried. A coating can then be additionally applied (coated granules) that allows the herbicide to be released at a controlled rate over a specific period of time.

The compounds of formula I may be used as herbicides in unmodified form, i.e. as obtained in the synthesis. They are preferably processed in conventional manner to emulsifiable concentrates, directly sprayable or dilutable solutions, dilute emulsions, wettable powders, soluble powders, dusts, granulates or microcapsules with the formulation assistants customarily employed in formulation technology. Such formulations are described, for example, in WO 97/34485, pages 9 to 12. As with the type of agents, the methods of application such as spraying, dusting, wetting, scattering or pouring, are selected in accordance with the intended objectives and the prevailing circumstances.

The formulations, i.e. the agents, preparations, or compositions comprising the compound of formula I or at least one compound of formula I and usually one or more than one liquid or solid formulation assistant, are prepared in known manner, e.g. by homogeneously mixing and/or grinding the herbicide with said formulation assistants, typically solvents or solid carriers. Surface-active compounds (surfactants) may additionally be used for preparing the formulations. Examples of solvents and solid carriers are described in said WO 97/34485, page 6.

Depending on the herbicide of formula I to be formulated, suitable surface-active compounds are nonionic, cationic and/or anionic surfactants and surfactant mixtures having good emulsifying, dispersing and wetting properties. Examples of suitable anionic, nonionic, and cationic surfactants are listed in said WO 97/34485, pages 7 and 8. Also the surfactants customarily used for the art of formulation and described, inter alia, in "Mc Cutcheon's Detergents and Emulsifiers Annual" MC Publishing Corp., Ridgewood N.J. 1981, Stache, H., "Tensid-Taschenbuch" (Handbook of Surfactants), Carl Hanser Verlag, Munich/Vienna, 1981, and M. and J. Ash, "Encyclopedia of Surfactants", Vol I–III, Chemical Publishing Co., New York, 1980–81 are suitable for manufacture of the herbicides according to the invention.

The herbicidal compositions will as a rule contain from 0.1 to 99% by weight, preferably from 0.1 to 95% by weight, of herbicide, from 1 to 99.9% by weight, preferably from 5 to 99.8% by weight, of a solid or liquid adjuvant, and from 0 to 25% by weight, preferably from 0.1 to 25% by weight, of a surfactant. Whereas it is preferred to formulate commercial products as concentrates, the end user will normally use dilute formulations. The compositions may also contain further ingredients, such as: stabilisers, e.g. where appropriate epoxidised vegetable oils (epoxidised coconut oil, rapeseed oil, or soybean oil); antifoams, typically silicone oil; preservatives; viscosity regulators; binders; and tackifiers; as well as fertilisers or other chemical agents.

The compounds of formula I are usually applied with success to the plants or the locus thereof in rates of application of 0.001 to 4 kg/ha, preferably 0.005 to 2 kg/ha. The rate of application required to achieve the desired action can be determined by experimentation. It will depend on the type of action, the development stage of the cultivated plant and of the weed, as well as on the application (locus, time, method), and as a result of these variables can vary over a wide range.

The compounds of formula I have excellent herbicidal and growth inhibiting properties, which make them suitable for application in crops of cultivated plants, especially in cereals, cotton, soybeans, sugar beet, sugar cane, plantations, rape, maize, and rice, and for the non-selective control of weeds. Crops will also be understood as meaning those crops that have been made tolerant to herbicides or classes of herbicides by conventional breeding or genetic engineering methods. The weeds to be controlled may be monocot as well as dicot weeds, typically *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola,* and *Veronica*.

The invention is illustrated by the following non-limitative Examples.

PREPARATIVE EXAMPLES

Example 1

Preparation of:
3-(2.6-dimethoxyphenoxy-1-(3-phenylacetonitrile) propyne (1)

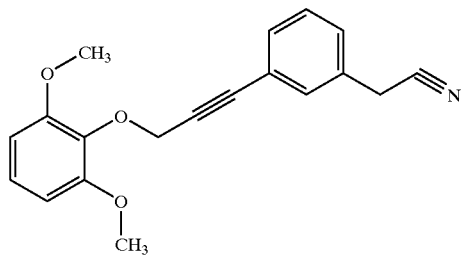

Step 1 Preparation of:
2,6-dimethoxy-O-propargyl phenol ether (1a)

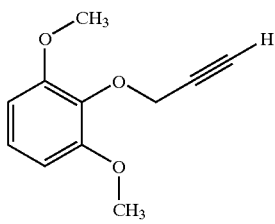

2,6-dimethoxyphenol (2.59 g) and potassium carbonate (2.30 g) are suspended in acetone (95 ml). Then propargyl bromide (5.00 g) is added dropwise with stirring at reflux temperature (56° C.) followed by stirring for 2.5 hours. The reaction is monitored by TLC (thin-layer chromatography, 10% ethyl acetate/n-hexane as eluant) on silica gel. The brown yellow mixture after reaction completion is filtered and then concentrated to an oil which is then chromatographed on silica gel with ethyl acetate/n-hexane elution (1:9). Evaporation of solvent gives the product (3.25 g, 99%) as a pure yellow oil. NMR (CDC$_{l3}$): 7.08–6.55 (m, 3H); 4.70 (d, 2H); 3.82 (s, 6H), 2.45 (t, 1H).

Step 2 Preparation of:

3-(2,6-dimethoxyphenoxy)-1-(3-phenylacetonitrile) propyne (1)

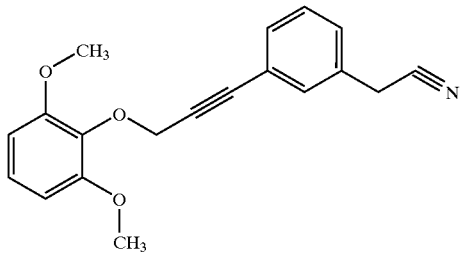

A catalyst mixture consisting of palladium tetrakis triphenylphosphine (116 mg), copper (I) iodide (15 mg) is dissolved in piperidine followed by addition of a solution of 2,6-dimethoxy-O-propargyl phenol ether (1) (420 mg) in piperidine (2 ml) at room temperature under nitrogen atmosphere. After stirring 10 minutes a solution of 3-iodo-1-phenylacetonitrile (505 mg) in piperidine (2 ml) is added. An immediate exothermic reaction (40° C.) is observed with subsequent cooling to room temperature accompanied by the formation of a thick suspension. Stirring is continued for 2–3 hours while the reaction is monitored by TLC (20% ethyl acetate/n-hexane) on silica gel. Then a saturated solution of ammonium chloride (40 ml) is added and subsequently extracted with diethyl ether (2×40 ml) followed by drying the organic phase over sodium sulfate. Evaporation of the filtered solution gives a dark brown residue which is triturated with diethylether to give a precipitate which is removed by filtration. The filtrate was then evaporated and the resulting oil is chromatographed on silica gel with n-hexane/ethyl acetate elution (9:1). Evaporation and drying under high vacuum gives the desired product as a pure product (304 mg, 49% yield) in the form of a brown resin. NMR (CDCl$_3$): 7.20–7.38 (m, 4H ), 7.00 (t, 1H), 6.58 (d, 2 H); 4.90 (s, 2H): 3.87 (s, 6H); 3.70 (s, 2H).

Example 2

Preparation of:

3-(2-trifluoromethoxyphenoxy)-1-(3-phenylacetonitrile) propyne (2)

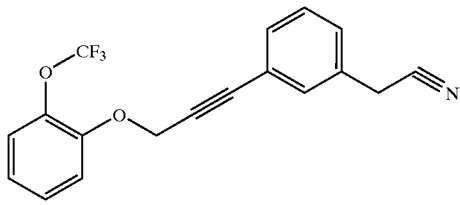

Step 1 Prepration of:
3-(2-trifluoromethoxy)-O-propargyl phenol ether (2a)

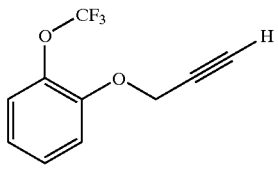

3-trifluoromethoxy phenol (2.99 g) and potassium carbonate (2.30 g) are suspended in acetone (95 mL). Then propargyl bromide (5.00 g) is added dropwise with stirring at reflux temperature (56° C.) followed by stirring for 2.5 hours. The reaction is monitored by TLC (10% ethyl acetate/n-hexane) on silica gel. The cooled mixture after reaction completion is filtered and then concentrated to an oil which is then chromatographed on silica gel with ethyl acetate/n-hexane elution (1:9). Evaporation of solvent gives the product (2.65 g, 73%) as a pure yellow oil. NMR (CDCl$_3$): 7.30–6.91 (m, 4H), 4.75 (d, 2H), 2.51 (t, 1H).

Step 2 Preparation of:
3-(2-trifluoromethoxyphenoxy)-1-(3-phenylacetonitrile) propyne (2)

A catalyst mixture consisting of palladium tetrakis triphenylphosphine (118 mg), copper (I) iodide (15 mg) is added to a solution of 3-iodo-1-phenylacetonitrile (500 mg) in piperidine (3 ml) at room temperature under nitrogen atmosphere. After stirring 30 minutes a solution of 3-(2-trifluromethoxy)-O-propargyl phenol ether (2a) (444 mg) in piperidine (2 ml) is added. An immediate exothermic reaction (35° C.) is observed with subsequent cooling to room temperature. Stirring is continued for 4 hours while the reaction is monitored by TLC (20% ethyl acetate/n-hexane) on silica gel. Then a saturated solution of ammonium chloride (40 ml) is added and subsequently extracted with ethyl acetate (2×20 ml) followed by drying the organic phase over sodium sulfate. Evaporation of the filtered solution gives a dark brown resin which is triturated with diethylether to give a precipitate which is removed by filtration. The filtrate was then evaporated and the resulting oil is chromatographed on silica gel with n-hexane/ethyl acetate (9:1) elution. Evaporation and drying under high vacuum gave the desired product as a pure product (430 mg, 63% yield) in the form of a yellow oil. NMR (CDCl$_3$): 7.40–6.90 (m, 8H), 6.74 (d,1H), 6.60 (d, 1H); 5.00 (s, 2H); 3.72 (s, 2H).

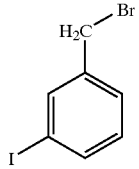

Preparation of: 3-iodo-1-alpha Bromo Toluene (2b)

3-iodo-toluene (65.4 g), N-bromosuccinimide (53.4 g) was dissolved in carbon tetrachloride (200 ml) and heated to reflux temperature under irradiation with 120 W tungsten lamp. . Then azoisobutyronitrile (100 mg) and dibenzoyl peroxide (100 mg) was added with continued stirring at reflux overnight (12 hours). Although the mixture still showed some trace amounts of starting material by TLC (20% ethyl acetate/n-hexane), the cooled reaction mixture was worked up. The filtered reaction solution was successively washed with water, aqueous sodium bicarbonate and brine and then dried over sodium sulfate. Filtration and evaporation gave an oil which was purified by silica gel chromatography with ethyl acetate/n-hexane elution. The yield was 65.2 g, 73% yield. NMR (CDCl$_3$): 7.91–7.00 (m, 3H), 6.50 (s, 1H), 4.40 (s, 2H).

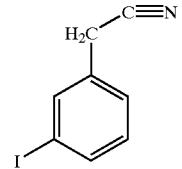

Preparation of: 3-iodo-1-phenylacetonitrile (2c)

The foregoing product (2b) (65.2 g) was dissolved in toluene (238 ml) containing sodium cyanide (11.8 g), tetra-n-butyl benzylammonium bromide (1.0 g) and water (20 ml). The solution was warmed to 50° C. and stirred vigorously for 12 hours. TLC monitor (20% ethyl acetate/n-hexane) showed the reaction still incomplete and sodium cyanide (5.0 g) and water (20 ml) was added with continued stirring. After an additional 6 hours the reaction was worked up by washing in water and subsequently drying over sodium sulfate. Filtration and evaporation gave a crude oil which was purified by silica gel column chromatography to give 30.6 g, 57% yield. NMR (CDCl$_3$): 7.65–7.20 (m,3H), 7.10 (s,1H), 3.70 (s,2 H).

Example 3

Preparation of:
3-(2-methoxyphenoxy)-1-(2-chloro-4-aminophenyl) propyne (3)

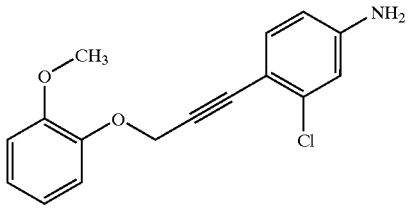

Step 1 Preparation of: 3-(2-methoxy)-O-propargyl phenol ether (3a)

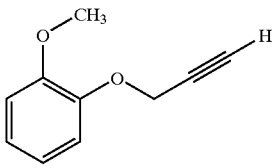

2-Methoxy phenol (4.17 g) and potassium carbonate (4.64 g) are suspended in acetone (95 ml). Then propargyl bromide (10.00 g) is added dropwise with stirring at reflux temperature (56° C.) followed by stirring for 2.5 hours. The reaction was regularly monitored by TLC (10% ethyl acetate/n-hexane). The cooled mixture after reaction completion is filtered and then concentrated to an oil which is then chromatographed on silica gel with ethyl acetate/n-hexane elution (1:9). Evaporation of solvent gives the product (2.65 g, 89%) as a oil. NMR (CDCl$_3$): 6.70–7.05 (m, 4H); 4.75 (d, 2H); 4.65 (t, 1H); 3.85 (s, 3H), 2.50 (t, 1H).

Step 2 Preparation of:
3-(2-methoxyphenoxy)-1-(2-chloro-4-aminophenyl) propyne (3)

A catalyst mixture consisting of palladium tetrakis triphenylphosphine (116 mg), copper (I) iodide (15 mg) is added to a solution of 3,5-dichloro-1-iodobenzene (506 mg) in piperidine (2 ml) at room temperature under nitrogen atmosphere. After stirring 10 minutes a solution of 3-(2- methoxy)-O-propargyl phenol ether (3a) (324 mg) in piperidine (2 ml) is added. An immediate exothermic reaction (40° C.) is observed with subsequent cooling to room temperature accompanied by the formation of a thick suspension. Stirring is continued for 2–3 hours while the reaction is monitored by TLC (20% ethyl acetate/n-hexane) on silica gel. Then a saturated solution of ammonium chloride (40 ml) is added and subsequently extracted with diethyl ether (2×40 ml) followed by drying the organic phase over sodium sulfate. Evaporation of the filtered solution gives a dark brown resin which is triturated with diethylether to give a precipitate which is removed by filtration. The filtrate was then evaporated and the resulting oil is chromatographed on silica gel with n-hexane/ethyl acetate elution. Evaporation and drying under high vacuum gives the desired product as a pure product (232 mg, 40% yield) in the form of a yellow oil. NMR (DMSO):7,2 (s, 1H ), 6.8–7.08 (m, 5H), 6.65–6.71 (d, 1H); 6.75 (NH) (s, 2H), 4.90 (s, 2H); 3,7 (s, 3H); 6.80–7.71 (m, 6H); 5.05 (s, 2H); 2.49 (s, 2H).

The following compounds are prepared in a manner analog to the above described.

TABLE 1

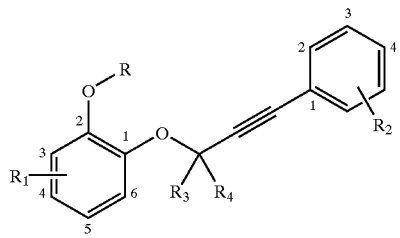

| Comp No. | $R_1$ | $R_2$ | R | $R_3/R_4$ | $^1$H-NMR (CDCl$_3$) or M.P./M.S. data |
|---|---|---|---|---|---|
| 1.001 | 4-CH2CN, 6-OCH3 | 4-Cl | CH3 | H/H | |
| 1.002 | 4-CH2CN, 6-OCH3 | 3-Cl | CH3 | H/H | |
| 1.003 | 4-CH2CN, 6-OCH3 | 3-Br | CH3 | H/H | MS 386 (97) |
| 1.004 | 4-CH2CN, 6-OCH3 | 3,4,5-tri-OCH3 | CH3 | CH3/H | MS 298 (95) |
| 1.005 | 6-OCH3 | 3-CN, 4-F | CH3 | H/H | |
| 1.006 | 6-OCH3 | 3-CN | CH3 | H/H | |
| 1.007 | 6-OCH3 | 3-NH2 | CH3 | H/H | |
| 1.008 | 4-CH2CN, 6-OCH3 | 3-N-phthalimide | CH3 | H/H | MS 467 (97) |
| 1.009 | 4-CH2CN, 6-OCH3 | 4-OCH3 | CH3 | H/H | MS 338 (99) |
| 1.010 | 4-CH2CN, 6-OCH3 | 3-CF3, 4-NHC(=O)CH3 | CH3 | H/H | MS 433 (94) |
| 1.011 | 6-OCH3 | 3-CH2Br | CH3 | H/H | |
| 1.012 | 6-OCH3 | 3-CH2CN | CH3 | H/H | 7.22–7.40 (m, 4H ) 7.02–7.09 (t, 1H) 6.58–6.63 (d, 2H) 4.92 (s, 2H) 3.87 (s, 6H) 3.70 (s, 2H) |
| 1.013 | 4-CH2CN, 6-OCH3 | 4-OCF3 | CH3 | CH3/H | |
| 1.014 | 6-OCH3 | 3-OS(O2)CH3 | CH3 | H/H | |
| 1.015 | 4-CH2CH=CH2 6-OCH3 | 3-CH2CN | CH3 | H/H | 7.20–7.40 (m, 4H), 6.40–(s, 2H) 5.95 (m, 1H) 5.15 (m, 2H) 4.85 (s, 2H), 3.83 (s, 6H) 3.70 (s, 2H) 3.30 (d, 2H) |
| 1.016 | 4-CH2CN, 6-OCH3 | 2-OCH3 | CH3 | H/H | |
| 1.017 | 4-CH2CN, 6-OCH3 | 3-CH2CN | CH3 | H/H | |
| 1.018 | 4-CH2CN, 6-OCH3 | 2-CH2OH | CH3 | H/H | MS 338 (93) |
| 1.019 | 6-OCH3 | 3-t-butyl | CH3 | H/H | |
| 1.020 | 6-OCH3 | 3-C(CH3)2CN | CH3 | H/H | |
| 1.021 | 6-OCH3 | 3-CH(CH3)CN | CH3 | H/H | |
| 1.022 | 6-OCH3 | 3-CH2CN | —CH$_2$CN | CH3/H | |
| 1.023 | 6-OCH3 | 4-CH3 | CH3 | H/H | |
| 1.024 | 6-OCH3 | 3-CH2CN | —COCH3 | H/H | |
| 1.025 | 6-OCH3 | 3-CH2CN | ethyl | H/H | |
| 1.026 | H | 3-F, 4-NH2 | CH3 | H/H | (d6-DMSO): 7.00–7.25 (m, 6H) 6.80–6.90 (t, 1H) 5.77 (1s, H)(s, 2H) 5.10 (s, 2H) 3.90 (s, 3H) |
| 1.027 | H | 3-CH3, 4-OH | CH3 | H/H | |

TABLE 1-continued

| Comp No. | R₁ | R₂ | R | R₃/R₄ | ¹H-NMR (CDCl₃) or M.P./M.S. data |
|---|---|---|---|---|---|
| 1.028 | H | 3-CF3 | CH3 | H/H | 7.50–7.60 (q, 4H), 6.90–7.12 (m, 4H), 5.01 (s, 2H) 3.90 (s, 3H) |
| 1.029 | H | 2-NH2 | CH3 | H/H | (d6-DMSO): 6.93–7.25 (m, 6H) 6.70–6.77 (d, 1H) 6.50–6.60 (t H) 5.40 (NH, s, 2H) 5.11 (s, 2H) 3.84 (s, 3H) |
| 1.030 | H | 3-CN | CH3 | H/H | |
| 1.031 | H | 4-CH2CO2CH3 | CH3 | H/H | 6.80–7.35 (m, 7H), 4.98 (s, 2H), 3.88 (s, 3H), 3.65 (s, 3H), 3.60 (s, 2H) |
| 1.032 | H | 3-CN | CH3 | H/H | |
| 1.033 | H | 3-CH2CN | CH3 | H/H | 6.90–7.42 (m, 8H) 4.98 (s, 2H) 3.90 (s, 3H) 3.20 (s, 2H) |
| 1.034 | H | 3-Cl, 4-NH2 | CH3 | H/H | (d6-DMSO): 7.20 (s, 1H) 6.80–7.08 (m, 5H) 6.65–6.71 (d, 1H) 6.75 (1H) (s, 2H) 4.90 (s, 2H) 3.70 (s, 3H) |
| 1.035 | H | 4-OH | CH3 | H/H | MS 255 (100) |
| 1.036 | H | 3-CH3 | CH3 | H/H | (d6-DMSO) 9.60 (s, 1H) 6.68–7.00 (m, 6H) 6.55–6.60(d, 1H) 4.75 (s, 2H) 3.58 (s, 3H) 1.90 (s, 3H) |
| 1.037 | H | 4-i-propyl | CH3 | H/H | MS 281 (99) |
| 1.038 | H | 4-OCHF2 | CH3 | H/H | MS 305 (100) |
| 1.039 | H | 3-CH2NH2 | CH3 | H/H | MS 268 (95) |
| 1.040 | H | 3,4,5-tri-OCH3 | CH3 | H/H | MS 329 (91) |
| 1.041 | H | 2,3-di-CH3 | CH3 | H/H | |
| 1.042 | H | 3,5-di-Cl | CH3 | H/H | MS 307 (92) |
| 1.043 | H | 3-CF3, 4-NHC(=O)CH3 | CH3 | H/H | |
| 1.044 | H | 3-CH2OH | CH3 | H/H | MS 269 (94) |
| 1.045 | H | 2-OCH3 | CH3 | H/H | MS 269 (98) |
| 1.046 | H | 2-Cl | CH3 | H/H | MS 271 (90) |
| 1.047 | H | 3-CN | CH3 | H/H | |
| 1.048 | H | 4-n-propyl | CH3 | H/H | MS 281 (98) |
| 1.049 | H | 2,3,4,5-tetra-CH3 | CH3 | H/H | MS 295 (100) |
| 1.050 | H | 2-OCH3, 5-Cl | CH3 | H/H | MS 303 (91) |
| 1.051 | H | 2,4,5-tri-Cl | CH3 | H/H | MS 341 (100) |
| 1.052 | H | 4-NH2 | CH3 | H/H | (d6-DMSO): 6.69–6.95 (m, 6H) 6.30–6.37(d, 2H) 5.45 (1H) (s, 2H) 4.75 (s, 2H) 3.60 (s, 3H) |
| 1.053 | H | 3-N-phthalimide | CH3 | H/H | MS 398 (85) |
| 1.054 | H | 4-OCH3 | CH3 | H/H | 6.75–7.38 (m, 8H), 5.00 (s, 2H), 3.80 (s, 3H), 3.75 (s, 3H) |
| 1.055 | H | 3-Br | CH3 | H/H | |
| 1.056 | H | 2-CN, 3-F | CH3 | H/H | |
| 1.057 | H | 3-CH2Br | CH3 | H/H | |
| 1.058 | H | 4-OCF3 | CH3 | H/H | |
| 1.059 | H | 2-CH2CN | CH3 | H/H | MS 278 (100) |
| 1.060 | 3-CH2- to R at position 2 | 3-CH2CN | —C(CH3)2— to R1 at position 3 | H/H | 7.20–7.40 and 6.70–6.85, m, 7H) 4.95 (s, 2H) 3.70 (s, 2H) 3.00 (s, 2H) 1.50 (s, 6H) |
| 1.061 | H | 3-OS(O2)CH3 | CH3 | H/H | |
| 1.062 | H | 3-CH3, 4-OCH3 | CH3 | H/H | |

TABLE 1-continued

| Comp No. | R₁ | R₂ | R | R₃/R₄ | ¹H-NMR (CDCl₃) or M.P./M.S. data |
|---|---|---|---|---|---|
| 1.063 | H | 3-CH2CN | SO2CH3 | CH₃/H | |
| 1.064 | H | 3-CH2CH2CN | CH3 | H/H | 6.88–7.35 (m, 8H), 4.98 (s, 2H), 3.88 (s, 3H), 2.93 (t, 2H), 2.62 (t, 2H) |
| 1.065 | H | 3-CH2CN | CF3 | H/H | 7.20–7.43 (m, 7H), 6.97–7.06 (dt, 1H), 5.00 (s, 2H), 3.72 (s, 2H) |
| 1.066 | H | 3-CH2CN | CF3 | CH₃/H | |
| 1.067 | H | 3-t-butyl | CH3 | H/H | |
| 1.068 | H | 2-CH3, 4-NO2 | CH3 | H/H | MS 297 (92) |
| 1.069 | H | 2-C(=O)NHCH2—CO2H | CH3 | H/H | |
| 1.070 | H | 3-F, 5-NO2 | CH3 | H/H | MS 300 (100) |
| 1.071 | H | 4-C(=O)CH3 | CH3 | H/H | MS 281 (97) |
| 1.072 | H | 3-OH | CH3 | H/H | MS 255 (100) |
| 1.073 | H | 4-t-butyl | CH3 | H/H | MS 295 (90) |
| 1.074 | H | 4-Cl | CH3 | H/H | MS 271 (92) |
| 1.075 | H | 3-C(CH3)2CN | CH3 | H/H | 6.90–7.49 (m, 8H) 4.98 (s, 2H) 3.85 (s, 3H) 1.70 (s, 6H) |
| 1.076 | H | 3-CH(CH3)CN | CH3 | H/H | |
| 1.077 | H | 2-CO2CH3 | CH3 | H/H | MS 297 (93) |
| 1.078 | H | 3-CO2H, 4-NH2 | CH3 | H/H | |
| 1.079 | H | 3-CH2CN | H | CH3/H | |
| 1.080 | H | 2-NH2 | CH3 | H/H | |
| 1.081 | H | 3-CH2CN | ethyl | H/H | 6.80–7.50 (m, 8H) 5.00 (s, 2H) 4.10 (q, 2H) 3.70 (s, 2H) 1.49 (t, 3H) |
| 1.082 | H | 3,4-di-Cl | CH3 | H/H | MS 307 (83) |
| 1.083 | H | 4-CH2CN | —CH₂CN | H/H | |
| 1.084 | H | 3-CH2CN | t-butyl | H/H | |
| 1.085 | H | 4-n-butyl | CH3 | CH3/CH3 | |
| 1.086 | H | 4-n-butyl | CH3 | H/H | MS 295 (100) |
| 1.087 | H | 4-CO2CH3 | CH3 | H/H | MS 295 (88) |
| 1.088 | H | 2,3-di-OCH3 5-CHO | CH3 | H/H | |
| 1.089 | H | 4-OCH2-phenyl | CH3 | H/H | MS 345 (100) |
| 1.090 | H | 4-CF3 | CH3 | H/H | MS 307 (100) |
| 1.091 | H | 3-CH2CN | phenyl | H/H | |
| 1.092 | H | 4-SCH3 | CH3 | H/H | |
| 1.093 | H | 3-CH2CN | i-propyl | H/H | |
| 1.094 | H | 3,4-(OCH2)2 | CH3 | H/H | |
| 1.095 | 4-CN | 3-Cl | CH3 | H/H | MS 298 (98) |
| 1.096 | 4-CN | 3,4-di-Cl | CH3 | H/H | |
| 1.097 | 4-CN | 4-NO2 | CH3 | H/H | |
| 1.098 | 4-CN | 4-Cl | CH3 | H/H | 7.10–7.35 (m, 7H) 5.03 (s, 2H) 3.90 (s, 3H) |
| 1.099 | 4-CN | 4-OCF3 | CH3 | H/H | MS 348 (97) |
| 1.100 | 4-CN | 2-CN | CH3 | H/H | |
| 1.101 | 4-CN | 3-CN | CH3 | H/H | 174–175° C. |
| 1.102 | 4-CN | 4-NH2 | CH3 | H/H | |
| 1.103 | 4-CN | 3-N-phthalimide | CH3 | H/H | MS 423 (92) |
| 1.104 | 4-CN | 3-Br | CH3 | H/H | 7.06–7.55 (m, 7H) 5.03 (s, 2H) 3.90 (s, 3H) |
| 1.105 | 4-CN | 2-OCH3 | CH3 | H/H | |
| 1.106 | 4-CN | 3,4,5-tri-OCH3 | CH3 | H/H | |
| 1.107 | 4-CN | 3-CH2NH2 | CH3 | H/H | MS 293 (94) |
| 1.108 | 4-CN | 4-CH2CN | CH3 | H/H | |
| 1.109 | 4-CN | 3-CH2CN | CH3 | H/H | 7.05–7.40 (m, 7H) 5.03 (s, 2H) 3.92 (s, 3H) 3.71 (s, 2H) |
| 1.110 | 4-CN | 3,5-di-Cl | CH3 | H/H | |
| 1.111 | 4-CN | 3-OSO2CH3 | CH3 | H/H | |

TABLE 1-continued

| Comp No. | $R_1$ | $R_2$ | R | $R_3/R_4$ | $^1$H-NMR (CDCl$_3$) or M.P./M.S. data |
|---|---|---|---|---|---|
| 1.112 | 4-CN | 3-CF3, 4-NH(C═O)CH3 | CH3 | H/H | MS 389 (94) |
| 1.113 | 4-CN | 3-t-butyl | CH3 | H/H | |
| 1.114 | 4-CN | 3-C(CH3)2CN | CH3 | H/H | |
| 1.115 | 4-CN | 3-CH(CH3)CN | CH3 | H/H | |
| 1.116 | 4-CN | 3-CH2CN | H | H/H | |
| 1.117 | 4-CN | 3-CH2CN | ethyl | CH$_3$/CH$_3$ | |
| 1.118 | 4-CN | 4-C(═O)CH3 | CH3 | H/H | |
| 1.119 | 4-CN | 3-CH2CN | CH3 | CH$_3$/CH$_3$ | |
| 1.120 | 4-CN | 4-CH═NOCH3 | CH3 | H/H | |
| 1.121 | 4-CN | 4-F | CH3 | H/H | |
| 1.122 | 4-CN | 3-F | CH3 | H/H | |
| 1.123 | 4-CN | 3,4-di-F | CH3 | H/H | |
| 1.124 | 4-CN | 3-CF3 | CH3 | H/H | light brown crystal, 7.66–7.68 (bs, 1H) 7.56–7.62 (m, 2H) 7.4–7.50 (t, 1H) 7.3–7.35 (dd, 1H) 7.10–7.15 (t, 2H) 5.05 (s, 2H) 3.92 (s, 3H) |
| 1.125 | 4-CN | 3-CF3, 4-F | CH3 | H/H | |
| 1.126 | 4-CN | 4-NHC(═O)CH3 | CH3 | H/H | |
| 1.127 | 4-CN | 4-NHCO2CH3 | CH3 | H/H | |
| 1.128 | 4-CN | 4-NHCHO | CH3 | H/H | |
| 1.129 | 4-CN | 4-NHCO-phenyl | CH3 | H/H | |
| 1.130 | 4-CN | H | —CH2CN | H/H | |
| 1.131 | 4-CN | 3-CH(CH3)CN | CH3 | H/H | |
| 1.132 | 4-CH2CN | 4-1-propyl | CH3 | H/H | |
| 1.133 | 4-CH2CN | 4-OH | CH3 | H/H | |
| 1.134 | 4-CH2CN | 4-t-butyl | CH3 | H/H | MS 334 (100) |
| 1.135 | 4-CH2CN | 2-CO2CH3 | CH3 | H/H | MS 335 (89) |
| 1.136 | 4-CH2CN | 4-OCHF2 | CH3 | H/H | MS 344 (95) |
| 1.137 | 4-CH2CN | 3-CF3 | CH3 | H/H | |
| 1.138 | 4-CH2CN | 3-OH | CH3 | H/H | |
| 1.139 | 4-CH2CN | 2-OCH3, 5-Cl | CH3 | H/H | MS 342 (98) |
| 1.140 | 4-CH2CN | 3-F, 5-NO2 | CH3 | H/H | |
| 1.141 | 4-CH2CN | 4-CO2CH3 | CH3 | H/H | MS 335 (100) |
| 1.142 | 4-CH2CN | 2-Cl | CH3 | H/H | |
| 1.143 | 4-CH2CN | 2,3-di-OCH3, 5-CHO | CH3 | H/H | MS 366 (97) |
| 1.144 | 4-CH2CN | 3,5-di-CF3 | CH3 | H/H | |
| 1.145 | 4-CH2CN | 2-CH3, 4,5-di-Cl | CH3 | H/H | |
| 1.146 | 4-CH2CN | 4-C(═O)CH3 | CH3 | H/H | |
| 1.147 | 4-CH2CN | 2-OCH3, 5-CO2CH3 | CH3 | H/H | |
| 1.148 | 4-CH2CN | 2-O-(2,4-di-Cl-phenyl) | CH3 | H/H | MS 438 (100) |
| 1.149 | 4-CH2CN | 2-OCH3, 4-NO2 | CH3 | H/H | |
| 1.150 | 4-CH2CN | 4-OCH2-phenyl | CH3 | H/H | |
| 1.151 | 4-CH2CN | 2,4,5-tri-Cl | CH3 | H/H | MS 380 (100) |
| 1.152 | 4-CH2CN | 2,3,4,5-tetra-CH3 | CH3 | H/H | |
| 1.153 | 4-CH2CN | 4-n-butyl | CH3 | H/H | |
| 1.154 | 4-CH2CN | 3-CH2NH2 | CH3 | H/H | MS 307 (98) |
| 1.155 | 4-CH2CN | 3,5-di-Cl | CH3 | H/H | |
| 1.156 | 4-CH2CN | 4-CH2CN | CH3 | H/H | MS 317 (99) |
| 1.157 | 4-CH2CN | 3-CF3, 4-NHC(═O)CH3 | CH3 | H/H | MS 403 (86) |
| 1.158 | 4-CH2CN | 4-OCH3 | CH3 | H/H | |
| 1.159 | 4-CH2CN | 2-OCH3 | CH3 | H/H | MS 308 (99) |
| 1.160 | 4-CH2CN | 3,4,5-tri-OCH3 | CH3 | H/H | MS 368 (92) |
| 1.161 | 4-CH2CN | 3-N-phthalimide | CH3 | H/H | MS 437 (87) |
| 1.162 | 4-CH2CN | H | CH3 | H/H | 74–75° |
| 1.163 | 4-CH2CN | 4-n-propyl | CH3 | H/H | |
| 1.164 | 4-CH2CN | 3-Cl | CH3 | H/H | MS 310 (99) |

TABLE 1-continued

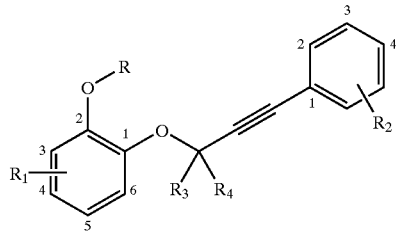

| Comp No. | $R_1$ | $R_2$ | R | $R_3/R_4$ | $^1$H-NMR (CDCl$_3$) or M.P./M.S. data |
|---|---|---|---|---|---|
| 1.165 | 4-CH2CN | 3-Br | CH3 | H/H | MS 356 (100) |
| 1.166 | 4-CH2CN | 3,4-di-Cl | CH3 | H/H | |
| 1.167 | 4-CH2CN | 4-CCF3 | CH3 | H/H | MS 362 (97) |
| 1.168 | 4-CH2CN | 3-CH2CN | CH3 | H/H | MS 317 (92) |
| 1.169 | 4-CH2CN | 4-Cl | CH3 | H/H | 108–109° C. |
| 1.170 | 4-CH2CN | 3,4-(OCH2)2 | CH3 | H/H | |
| 1.171 | 4-CH2CN | 2-CH2CN | CH3 | H/H | MS 317 (100) |
| 1.172 | 4-CH2CN | H | CHF2 | H/H | |
| 1.173 | 4-CH2CN | 4-CF3 | CH3 | H/H | |
| 1.174 | 4-CH2CN | 3-CH2CN | H | H/H | |
| 1.175 | 4-CH2CN | 4-n-propyl | CH3 | H/H | |
| 1.176 | 4-CH2CN | 3-Cl | phenyl | H/H | |
| 1.177 | 4-CH2CN | 4-Br | CH3 | H/H | 113–114° C. |
| 1.178 | 4-CH2CN | 3-Cl | CF3 | H/H | |
| 1.179 | 4-CH2CN | 4-F | CH3 | H/H | 3.71 (s, 2H), 3.90 (s, 3H) 4.97 (s, 2H) 6.8–7.1 (m, 5H) 7.30–7.45 (m, 2H) |
| 1.180 | 3-CN | 3-CF3 | CH3 | CH$_3$/CH$_3$ | |
| 1.181 | 3-CN | 3-Cl | CH3 | H/H | |
| 1.182 | 3-CN | 3-Cl | CH3 | CH$_3$/CH$_3$ | |
| 1.183 | 3-CN | 3-CH2CN | CH3 | CH$_3$/H | |
| 1.184 | 3-CH2CN | H | CH3 | H/H | |
| 1.185 | 3-CH2CN | 4-n-propyl | CH3 | H/H | |
| 1.186 | 3-CH2CN | 3-Cl | CH3 | H/H | |
| 1.187 | 3-CH2CN | 3-Br | CH3 | H/H | |
| 1.188 | 3-CH2CN | 3,4-di-Cl | CH3 | H/H | |
| 1.189 | 3-CH2CN | 4-CF3O | CH3 | H/H | |
| 1.190 | 3-CH2CN | 3-CH2CN | CH3 | H/H | |
| 1.191 | 4-NO2 | 4-CH2CN | CH3 | H/H | |
| 1.192 | 4-NO2 | 3-Br | CH3 | H/H | |
| 1.193 | 4-NO2 | 3,4-di-Cl | CH3 | H/H | |
| 1.194 | 4-NO2 | 3-CF3, 4-NHC(=O)CH3 | CH3 | H/H | MS 409 (85) |
| 1.195 | 4-NO2 | 3,5-di-Cl | CH3 | H/H | |
| 1.196 | 4-NO2 | 4-OCF3 | CH3 | H/H | MS 368 (100) |
| 1.197 | 4-NO2 | 4-Cl | CH3 | H/H | |
| 1.198 | 4-NO2 | 3-CH2CN | CH3 | H/H | MS 323 (92) |
| 1.199 | 4-NO2 | 3-Cl | CH3 | H/H | |
| 1.200 | 4-Br, 6-NO2 | 3-CH2CN | CH3 | H/H | |
| 1.201 | 4-CHO, 6-I | 3-CH2CN | CH3 | H/H | 7.90 (s, 1H) 7.40–7.70 (m, 6H) 5.10 (s, 2H) 3.95 (s, 3H) 3.72 (s, 2H) |
| 1.202 | 4-CH2CH=CH2 | 3-CH2CN | CH3 | H/H | |
| 1.203 | 4-CH=CH-NO2 | 3-CH2CN | CH3 | H/H | |
| 1.204 | 4-NH2 | 3-CH2CN | CH3 | H/H | 7.30–7.40 (m, 4H) 6.66, 6.40 (d ea, 1H ea) 6.15 (dd, 1H) 4.95 (s, 2H) 4.70 (br s, 2H) 4.05 (s, 2H), 3.65 (s, 3H) |
| 1.205 | 4-CHO, 6-NO2 | 3-CH2CN | CH3 | H/H | |
| 1.206 | 4-COCH3 | 3-CH2CN | CH3 | H/H | |
| 1.207 | 4-n-butyl | 3-CH2CN | CH3 | H/H | |
| 1.208 | 4-NO2, 6-CHO | 3-CH2CN | CH3 | H/H | |
| 1.209 | 4-n-propyl | 3-CH2CN | CH3 | H/H | |
| 1.210 | 3-NH2 | 3-CH2CN | CH3 | H/H | |
| 1.211 | 3-OCH3 | 3-CH2CN | CH3 | H/H | 6.50–7.50 (m, 7H) 4.95 (s, 2H) 3.85 (s, 3H) 3.82 (s, 3H) 3.70 (s, 2H) |
| 1.212 | 4-CH2CO2H | 3-CH2CN | CH3 | H/H | |
| 1.213 | 4-CO2H | 3-CH2CN | CH3 | H/H | |
| 1.214 | 4-CO2CH3 | 3-CH2CN | CH3 | H/H | |

TABLE 1-continued

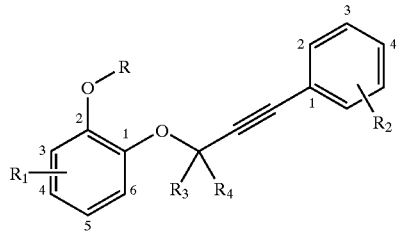

| Comp No. | $R_1$ | $R_2$ | R | $R_3/R_4$ | $^1$H-NMR (CDCl$_3$) or M.P./M.S. data |
|---|---|---|---|---|---|
| 1.215 | 5-CO2-n-hexyl | 3-CH2CN | CH3 | H/H | 7.05–7.70 (m, 7H) 5.02 (s, 2H) 4.25 (t, 2H) 3.80 (s, 3H) 3.68 (s, 2H) 1.70 (m, 2H) 1.25–1.49 (m, 6H) 0.90 (t, 3H) |
| 1.216 | 4-CH2NH2 | 3-CH2CN | CH3 | H/H | |
| 1.217 | 4-OH | 3-CH2CN | CH3 | H/H | |
| 1.218 | 6-F | 3-CH2CN | CH3 | H/H | |
| 1.219 | 6-F | 3-C(CH3)2CN | CH3 | H/H | |
| 1.220 | 6-F | 3-CH(CH3)CN | CH3 | H/H | |
| 1.221 | 5-F | 3-CH2CN | CH3 | H/H | |
| 1.222 | 5-F | 3-C(CH3)2CN | CH3 | H/H | |
| 1.223 | 5-F | 3-CH(CH3)CN | CH3 | H/H | |
| 1.224 | 4-F | 3-CH2CN | CH3 | H/H | 7.27–7.42 (m, 4H) 7.00–7.08 (q, 1H) 6.56–6.62 (m, 2H), 4.94 (s, 2H) 3.88 (s, 3H) 3.72 (s, 2H) |
| 1.225 | 4-F | 3-C(CH3)2CN | CH3 | H/H | light brown crystal, 6.55–6.74, 6.95–7.05, 7.30–7.50 (m, 7H), 4.95 (s, 2H) 3.85 (s, 3H), 1.65 (s, 6H) |
| 1.226 | 4-F | 3-CH(CH3)CN | CH3 | H/H | |
| 1.227 | 3-F | 3-CH2CN | CH3 | H/H | |
| 1.228 | 3-F | 3-C(CH3)2CN | CH3 | H/H | |
| 1.229 | 3-F | 3-CH(CH3)CN | CH3 | H/H | |
| 1.230 | 5-CH2OH | 3-CH2CN | CH3 | H/H | 6.85–7.40 (m, 7H) 4.98 (s, 2H) 4.65 (s, 2H) 3.80 (s, 3H) 3.70 (s, 1H) |
| 1.231 | 4-CO2CH3 | 3-CH2CN | CH3 | H/H | |
| 1.232 | 4-Br, 6-CHO | 3-CH2CN | CH3 | H/H | 7.55 (d, 1H) 7.20–7.30 (m, 5H) 5.05 (s, 2H) 3.80 (s, 3H) 3.70 (s, 2H) |
| 1.233 | 4-CHO | 3-CH2CN | CH3 | CH$_3$/H | |
| 1.234 | 4-CH=NOCH3 | 3-CH2CN | CH3 | H/H | |
| 1.235 | 6-phenyl | 3-CH2CN | CH3 | H/H | |
| 1.236 | 4-Cl | 3-CH2CN | CH3 | H/H | yellow solid, 7.30–7.40 (m, 4H) 7.00–7.05 (dd, 1H) 6.85–6.92 (m, 2H) 4.95 (s, 2H) 3.88 (s, 3H) 3.70 (s, 2H) |
| 1.237 | 4-Cl | 3-C(CH3)2CN | CH3 | H/H | |
| 1.238 | 4-Cl | 3-CH(CH3)CN | CH3 | H/H | |
| 1.239 | 3-Cl | 3-CH2CN | CH3 | H/H | |
| 1.240 | 3-Cl | 3-C(CH3)2CN | CH3 | H/H | |
| 1.241 | 3-Cl | 3-CH(CH3)CN | CH3 | H/H | |
| 1.242 | 5-Cl | 3-CH2CN | CH3 | H/H | |
| 1.243 | 5-Cl | 3-C(CH3)2CN | CH3 | H/H | |
| 1.244 | 5-Cl | 3-CH(CH3)CN | CH3 | H/H | |
| 1.245 | 6-Cl | 3-CH2CN | CH3 | H/H | |
| 1.246 | 6-Cl | 3-C(CH3)2CN | CH3 | H/H | |
| 1.247 | 6-Cl | 3-CH(CH3)CN | CH3 | H/H | |
| 1.248 | 4-ethyl | 3-CH2CN | CH3 | H/H | |
| 1.249 | 5-CN | 3-CH2CN | CH3 | H/H | |
| 1.250 | 6-CN | 3-CH2CN | CH3 | H/H | |
| 1.251 | 3-OS(O2)CH3 | 3-CH2CN | CH3 | H/H | |
| 1.252 | 4-OS(O2)CH3 | 3-CH2CN | CH3 | H/H | |
| 1.253 | 5-OS(O2)CH3 | 3-CH2CN | CH3 | H/H | |
| 1.254 | 6-OS(O2)CH3 | 3-CH2CN | CH3 | H/H | |
| 1.255 | 5-CH=NOCH3 | 3-CH2CN | CH3 | H/H | |
| 1.256 | 6-CH=NOCH3 | 3-CH2CN | CH3 | H/H | |
| 1.257 | 4-CH=NOCH3 | 4-Cl | CH3 | H/H | 103–104° C. |
| 1.258 | 4-C(CH3)=NOCH3 | 4-Cl | CH3 | H/H | |
| 1.259 | 4-CH=NOCH3 | 3-Cl | CH3 | H/H | |

TABLE 1-continued

| Comp No. | R₁ | R₂ | R | R₃/R₄ | ¹H-NMR (CDCl₃) or M.P./M.S. data |
|---|---|---|---|---|---|
| 1.260 | 4-C(CH3)=NOCH3 | 3-Cl | CH3 | H/H | |
| 1.261 | 4-CH=NOCH3 | 3-CH2CN | CH3 | H/H | |
| 1.262 | 4-C(CH3)=NOCH3 | 3-CH2CN | CH3 | H/H | |
| 1.263 | 4-CN | 3-CH=NOCH3 | CH3 | H/H | |
| 1.264 | 4-CN | 4-C(CH3)=NOCH3 | CH3 | H/H | |
| 1.265 | 4-C(CH3)=NOCH3 | 3-Cl | CH3 | H/H | |
| 1.266 | 4-Br | 4-Cl | CH3 | H/H | 82–83° C. |
| 1.267 | 4-COCH3 | 4-Cl | CH3 | H/H | 92–94° C. |
| 1.268 | 4-C(CH3)=NOCH3 | 4-Cl | CH3 | H/H | 102–103° C. |
| 1.269 | 4-(CH₂)₂CONH₂ | 4-Cl | CH3 | H/H | 188–192° C. |
| 1.270 | 4-(CH₂)₂CO₂CH₃ | 4-Cl | CH3 | H/H | 2.63 (t, 2H) 2.91 (t, 2H) 3.67 (s, 3H) 3.87 (s, 3H) 4.93 (s, 2H) 6.70–6.80 (m, 2H) 7.00 (d, 1H) 7.20–7.40 (m, 4H) |
| 1.271 | 4-F | 3-Cl | CH3 | H/H | brown solid, 6.55–6.70, 6.95–7.05, 7.00–7.39 (m, 7H), 4.92 (s, 2H) 3.85 (s, 3H) |
| 1.272 | 4-F | 4-Cl | CH3 | H/H | light brown crystal, 6.50–6.70, 6.95–7.05, 7.00–7.35 (m, 7H), 4.90 (s, 2H) 3.85 (s, 3H) |
| 1.273 | 4-F | 3-Br | CH3 | H/H | light brown crystal, 6.50–6.70, 6.90–7.50 (m, 7H), 4.90 (s, 2H) 3.85 (s, 3H) |
| 1.274 | 4-F | 3-CN | CH3 | H/H | |
| 1.275 | 4-F | 4-CN | CH3 | H/H | |
| 1.276 | 4-CN | 3-CH2CH2CN | CH3 | H/H | 7.21–7.37 (m, 6H), 7.16 (s, 1H), 5.04 (s, 2H), 3.94 (s, 3H), 2.93 (t, 2H), 2.62 (t, 2H) |
| 1.277 | H | 3-CH2CH2CN | CH3 | H/H | 6.88–7.35 (m, 8H), 4.98 (s, 2H), 3.88 (s, 3H), 2.93 (t, 2H), 2.62 (t, 2H) |
| 1.278 | 3-CH2CH2CN | 3-CN | CH3 | H/H | 118–119° C. |
| 1.279 | 3-CH2CH2CN | 4-Cl | CH3 | H/H | 100–101° C. |
| 1.280 | 4-(CH₂)₂NH₂.HCl | 4-Cl | CH3 | H/H | d6-DMSO: 2.8–2.9 (m, 2H) 2.95–3.05 (m, 2H) 3.79 (s, 3H) 4.98 (s, 2H) 6.79 (dd, 1H) 6.93 (d, 1H) 7.04 (d, 1H) 7.46 (s, 4H) 8.22 (br s, 3H) |
| 1.281 | 5-CN | 3-Cl | CH3 | H/H | |
| 1.282 | 5-CN | 4-Cl | CH3 | H/H | |
| 1.283 | 5-CN | 3-CH2CN | CH3 | H/H | |
| 1.284 | 5-CH2CN | 3-CN | CH3 | H/H | 118–119° C. |
| 1.285 | 5-CH2CN | 4-Cl | CH3 | H/H | 100–101° C. |
| 1.286 | 5-CH2CN | 3-Cl | CH3 | H/H | |
| 1.287 | 6-CH2CN | 3-CN | CH3 | H/H | |
| 1.288 | 6-CH2CN | 4-Cl | CH3 | H/H | |
| 1.289 | 6-CH2CN | 3-Cl | CH3 | H/H | |
| 1.290 | 6-CH2CN | 4-OCH3 | CH3 | H/H | |
| 1.291 | 4-F | 3-CHFCN | CH3 | H/H | 6.55–6.72, 6.96–7.04, 7.85–7.60, (m, 7H), 6.02 (d, 1H), 4.92 (s, 2H) 3.88 (s, 3H) |
| 1.292 | 4-F | 3-CF2CN | CH3 | H/H | white solid, 6.60–6.70, 7.01–7.10, 7.40–7.65 7.75–7.85 (m, 7H) 5.95 (s, 2H) 3.90 (s, 3H) |
| 1.293 | 4-F | 3-CH2CN | CH3 | CH3/H | yellow resin, 7.25–7.38 (m, 4H) 7.05–7.12 (q, 1H) 6.55–6.70 (m, 2H) 5.00– |

TABLE 1-continued

[Structure: benzene ring with OR at position 2 and O-C(R3)(R4)-C≡C-phenyl(R2) at position 1, R1 at position 4]

| Comp No. | R₁ | R₂ | R | R₃/R₄ | ¹H-NMR (CDCl₃) or M.P./M.S. data |
|---|---|---|---|---|---|
| | | | | | 5.12 (q, 1H) 3.88 (s, 3H) 3.72 (s, 2H) 1.72–1.79 (d, 3H) |
| 1.294 | 4-F | 3-CH2CN | CH3 | CH3/CH3 | |
| 1.295 | 4-F | 3-CH2C(=S)NH2 | CH3 | H/H | |
| 1.296 | 4-F | 2-OCH3,5-CH2CN | CH3 | H/H | |
| 1.297 | 4-F | 3-CH2CH=NOCH3 | CH3 | H/H | |
| 1.298 | 4-F | 3-CH(CN)n-pentyl | CH3 | H/H | |
| 1.299 | 4-F | 3,4-di-F | CH3 | H/H | yellow crystal, 6.98–7.30 (m, 4H) 6.58–6.70 (m, 2H) 4.90 (s, 2H) 3.89 (s, 3H) |
| 1.300 | 4-F | 4-F | CH3 | H/H | brown crystal, 7.35–7.42 (m, 2H) 6.93–7.06 (m, 3H) 6.55–6.72 (m, 2H) 4.92 (s, 2H) 3.88 (s, 3H) |
| 1.301 | 4-F | 3-F | CH3 | H/H | yellow crystal, 7.00–7.32 (m, 5H) 6.58–6.72 (m, 2H) 4.92 (s, 2H) 3.90 (s, 3H) |
| 1.302 | 4-(2-CF3 Phenyl-NHN=CH)— | 3-CH2CN | CH3 | H/H | |
| 1.303 | 4-CHO | 3-CH2CN | CH3 | H/H | |
| 1.304 | 4-Cl | 4-Cl | CH3 | H/H | yellow solid, 7.25–7.35 (dq, 4H) 7.00–7.05 (dd, 1H) 6.85–6.92 (m, 2H) 4.95 (s, 2H) 3.88 (s, 3H) |
| 1.305 | 4-Cl | 3-Cl | CH3 | H/H | yellow solid, 7.40 (ds, 1H) 7.2–7.35(m, 3H) 7.00–7.05 (dd, 1H) 6.90–6.95 (dd, 2H) 4.95 (s, 2H) 3.88 (s, 3H) |
| 1.306 | 4-Cl | 3-Br | CH3 | H/H | |
| 1.307 | 4-Cl | 4-F | CH3 | H/H | yellow crystal, 7.35–7.45 (m, 2H) 6.85–7.05 (m, 5H) 4.95 (s, 2H) 3.88 (s, 3H) |
| 1.308 | 4-Cl | 3-F | CH3 | H/H | white crystal, 7.00–7.35 (m, 5H) 6.87–6.94 (m, 2H) 4.95 (s, 2H) 3.88 (s, 3H) |
| 1.309 | 4-Cl | 4-OCHF2 | CH3 | H/H | yellow crystal, 7.38–7.45 (dd, 2H) 7.00–7.10 (m, 3H) 6.85–6.93 (m, 2H) 6.8 + 6.5 + 6.2 (3s, 1H) 4.95 (s, 2H) 3.88 (s, 3H) |
| 1.310 | 4-Cl | 3,4-di-Cl | CH3 | H/H | yellow crystal, 7.20–7.50 (m, 3H) 6.85–7.00 (m, 3H) 4.95 (s, 2H) 3.88 (s, 3H) |
| 1.311 | 4-Cl | 4-OCH2-phenyl | CH3 | H/H | yellow crystal, 7.30–7.45 (m, 7H) 7.00–7.06 (dd, 1H) 6.85–6.93 (m, 4H) 5.05 (s, 2H) 4.92 (s, 2H) 3.88 (s, 3H) |
| 1.312 | H | 3-CH2CN | —OCH₂O—(CH₂)₂O—CH₃ | H/H | 6.90–7.65 (m, 8H) 5.37 (s, 2H) 5.00 (s, 2H) 3.85 (t, 2H) 3.71 (s, 2H) 3.55 (t, 2H) 3.40 (s, 3.11) |
| 1.313 | H | 3-CH2CN | H | H/H | |
| 1.314 | H | 3-CF2CN | CH3 | H/H | |
| 1.315 | H | 3-CHFCN | CH3 | H/H | |

TABLE 1-continued

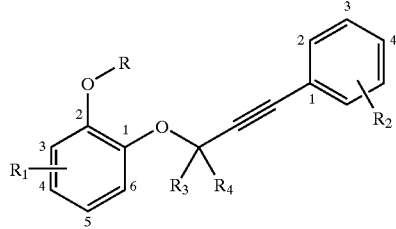

| Comp No. | R₁ | R₂ | R | R₃/R₄ | ¹H-NMR (CDCl₃) or M.P./M.S. data |
|---|---|---|---|---|---|
| 1.316 | H | 3-CF2CN | CH3 | CH3/H | |
| 1.317 | H | 3-CHFCN | CH3 | CH3/CH3 | |
| 1.318 | 4-CH(CH3)O—C(=O)CH3 | 3-CH2CN | CH3 | H/H | 7.40–6.91(m, 7H); 5.86 (q, 1H); 4.97 (s, 2H); 3.89 (s, 3H); 3.70 (s, 2H); 2.08 (s, 3H); 1.53 (d, 3H). |
| 1.319 | 4-CH(OH)CH3 | | CH3 | H/H | 7.40–6.91 (m, 7H) 4.97 (s, 2H) 4.87 (q, 1H); 3.89 (s, 3H) 3.72 (s, 2H) 2.00 (s, 1H); 1.50 (d, 3H). |
| 1.320 | 4-CH=NO-allyl | 3-CH2CN | CH3 | H/H | 8.00 (s, 1H); 7.48–7.03 (m, 7H) 6.20 (t, 1H); 5.00 (s, 2H) 4.74 (d, 2H); 3.94 (s, 3H) 3.73 (s, 2H) |
| 1.321 | 4-CH=NOCH₂ClC=CH₂ | 3-CH2CN | CH3 | H/H | 8.10 (s, 1H); 7.40–7.05 (m, 7H) 5.49 (s, 2H); 5.40 (s, 1H); 4.98 (s, 2H) 4.70 (s, 2H). 3.92 (s, 3H); 3.70 (s, 2H) |
| 1.322 | 4-CH=N—O-t-butyl | 3-CH2CN | CH3 | H/H | 8.00 (s, 1H); 7.46–7.00 (m, 7H); 5.00 (s, 2H); 3.93 (s, 3H); 3.70 (s, 2H); 1.34 (s, 9H). |
| 1.323 | 4-F | 3-CH2OCH3 | CH3 | H/H | 7.40–6.57 (m, 7H); 4.95 (s, 2H); 4.42 (s, 2H); 3.89 (s, 3H); 3.48 (s, 3H). |
| 1.324 | 4-CH=NO-ethyl | 3-Br | CH3 | H/H | 8.02 (s, 1H); 7.55–7.03 (s, 3H) 5.00 (s, 2H) 4.21 (q, 2H); 3.94 (s, 3H); 1.31 (t, 3H). |
| 1.325 | 4-C(CH3)=NOCH3 | 3-Cl | CH3 | H/H | 7.40–7.03 (m, 7H) 5.02 (s, 2H); 3.97 (s, 3H); 3.95 (s, 3H) 2.22 (s, 3H). |
| 1.326 | 4-CH=NOCH3 | 3-CH(CH3)CN | CH3 | H/H | 8.02 (s, 1H), 7.40–7.03 (m, 7H) 5.02 (s, 2H); 3.97 (s, 3H); 3.95 (s, 3H) 3.87 (q, 1H); 1.61 (d, 3H). |
| 1.327 | 4-CH=NOCH3 | 3-(1-CN-cyclopropyl) | CH3 | H/H | 8.00 (s, 1H) 7.32–6.99 (m, 7H); 5.00 (s, 2H); 3.95 (s, 3H); 3.93 (s, 3H); 1.72 (t, 2H) 1.40 (t, 2H). |
| 1.328 | 4-F | 2-OCH3, 4-CH2CN | CH3 | H/H | m.p. 91–92 |
| 1.329 | 4-CN | 3-C(CH3)=NOCH3 | CH3 | H/H | 7.55–7.12 (m, 7H); 5.03 (s, 2H); 3.92 (s, 3H) 3.85 (s, 3H); 2.16 (s, 3H). |
| 1.330 | 4-CN | 3-C(=O)N(OCH3)—CH3 | CH3 | H/H | 7.73 (m, 7H); 5.05 (s, 2H) 3.92 (s, 3H); 3.53 (s, 3H); 3.36 (s, 3H) |
| 1.331 | 5-CH=NOCH3 | 3-Cl | CH3 | H/H | 8.03 (s, 1H); 7.50–6.88 (m, 7H); 5.02 (s, 2H) 3.97 (s, 3H) 3.92 (s, 3H). |
| 1.332 | 4-C(CH3)=NOCH3 | 4-Cl | CH3 | H/H | 7.34–7.00 (m, 7H); 5.00 (s, 2H); 3.97 (s, 3H); 3.92 (s, 3H) ; 2.23 (s, 3H). |
| 1.333 | H | 3-CH2CH2CN | CH3 | H/H | 7.32–6.87 (m, 8H); 4.98 (s, 2H); 3.88 (s, 3H); 2.92 (t, 2H); 2.61 (t, 2H). |
| 1.334 | 4-CN | 3.CH2CH2CN | CH3 | H/H | 7.37–7.12 (m, 7H); 5.04 (s, 2H); 3.93 (s, 3H) 2.93 (t, 2H), 2.61 (t, 2H). |

TABLE 1-continued

| Comp No. | R₁ | R₂ | R | R₃/R₄ | ¹H-NMR (CDCl₃) or M.P./M.S. data |
|---|---|---|---|---|---|
| 1.335 | 5-CH2CN | 3-CN | CH3 | H/H | 7.72–6.87 (m, 7H); 5.00 (s, 2H), 3.89 (s, 3H) 3.73 (s, 2H). |
| 1.336 | 4-CH3 | 3-CH2CN | CH3 | H/H | yellow crystal, 7.25–7.40 (m, 4H) 6.96–7.01 (d, 1H) 6.70–6.77 (d, 2H) 4.95 (s, 2H) 3.88 (s, 3H) 3.77 (s, 2H) 2.32 (s, 3H) |
| 1.337 | 4-CH3 | 3-Cl | CH3 | H/H | white crystal, 7.40 (s, 1H) 7.27–7.33 (m, 3H) 6.95–7.00 (d, 1H) 6.7–6.75 (d, 2H) 4.95 (s, 2H) 3.88 (s, 3H) 2.32 (s, 3H) |
| 1.338 | 4-CH3 | 4-Cl | CH3 | H/H | light yellow crystal, 7.22–7.37 (m, 4H) 6.93–7.00 (d, 1H) 6.68–6.75 (d, 2H) 4.95 (s, 2H) 3.88 (s, 3H) 2.32 (s, 3H) |
| 1.339 | 4-CH3 | 3-Br | CH3 | H/H | |
| 1.340 | 4-CH3 | 2-OCH3, 5-CH2CN | CH3 | H/H | |
| 1.341 | 4-CH3 | 3-CH2CN | CH3 | CH3/H | |
| 1.342 | 4-CH3 | 3-CH(CH3)CN | CH3 | H/H | |
| 1.343 | 4-CH3 | 3-CH2C(=S)NH2 | CH3 | H/H | |
| 1.344 | 4-CH3 | 3-CH2CH=NOCH3 | CH3 | H/H | |
| 1.345 | 4-CF3 | 3-CH2CN | CH3 | H/H | light yellow solid, 7.20–7.40 (m, 5H) 7.10–7.16 (d, 2H) 5.02 (s, 2H) 3.94 (s, 3H) 3.70 (s, 3H) |
| 1.346 | 4-CF3 | 3-Cl | CH3 | H/H | white solid, 7.40 (s, 1H) 7.20–7.35 (m, 4H) 7.1–7.16 (d, 2H) 5.02 (s, 2H) 3.94 (s, 3H) |
| 1.347 | 4-CF3 | 4-Cl | CH3 | H/H | beige solid, 7.20–7.48 (m, 5H) 7.10–7.16 (d, 2H) 5.02 (s, 2H) 3,94 (s, 3H) |
| 1.348 | 4-CF3 | 3-Br | CH3 | H/H | white solid, 7.56 (s, 1H) 7.43–7.50 (d, 1H) 7.30–7.36 (d, 1H) 7.1–7.38 (m, 4H) 5.02 (s, 2H) 3.94 (s, 3H) |
| 1.349 | 4-CF3 | 2-OCH3,5-CH2CN | CH3 | H/H | |
| 1.350 | 4-CF3 | 3-CH2CN | CH3 | CH3/H | |
| 1.351 | 4-CF3 | 3-CH(CH3)CN | CH3 | H/H | |
| 1.352 | 4-CF3 | 3-CH2CN | CH3 | CH3/CH3 | |
| 1.353 | 4-CF3 | 3-CH2C(=S)NH2 | CH3 | H/H | |
| 1.354 | 4-CF3 | 3-CH2CH=NOCH3 | CH3 | H/H | |
| 1.355 | 4-ethyl | 3-CH2CN | CH3 | H/H | |
| 1.356 | 4-ethyl | 3-Cl | CH3 | H/H | |
| 1.357 | 4-ethyl | 4-Cl | CH3 | H/H | |
| 1.358 | 4-ethyl | 3-Br | CH3 | H/H | |
| 1.359 | 4-ethyl | 2-OCH3,5-CH2CN | CH3 | H/H | |
| 1.360 | 4-ethyl | 3-CH2CN | CH3 | CH3/H | |
| 1.361 | 4-ethyl | 3-CH(CH3)CN | CH3 | H/H | |
| 1.362 | 4-ethyl | 3-CHFCN | CH3 | H/H | |
| 1.363 | 4-ethyl | 3-CF2CN | CH3 | H/H | |
| 1.364 | 4-ethyl | 3-CH2C(=S)NH2 | CH3 | H/H | |
| 1.365 | 5-CH3 | 3-CH2CN | CH3 | H/H | |
| 1.366 | 5-CH3 | 3-Cl | CH3 | H/H | brown resin, 7.40 (s, 1H) 7.18–7.33 (m, 3H) 6.90 (s, 1H) 6.75–6.85 (m, 2H) 4.95 (s, 2H) 3.86 (s, 3H) 2.31 (s, 3H) |

TABLE 1-continued

| Comp No. | R₁ | R₂ | R | R₃/R₄ | ¹H-NMR (CDCl₃) or M.P./M.S. data |
|---|---|---|---|---|---|
| 1.367 | 5-CH3 | 4-Cl | CH3 | H/H | brown resin, 7.30–7.38 (d, 2H) 7.25–7.30 (d, 2H) 6.90 (s, 1H) 6.75–6.85 (m, 2H) 4.95 (s, 2H) 3.86 (s, 3H) 2.31 (s, 3H) |
| 1.368 | 5-CH3 | 3-Br | CH3 | H/H | dark yellow resin, 7.56 (s, 1H) 7.30–7.50 (dd, 2H) 7.10–7.20 (t, 1H) 6.90 (s, 1H) 6.75–6.85 (m, 2H) 4.95 (s, 2H) 3.86 (s, 3H) 2.31 (s, 3H) |
| 1.369 | 5-CH3 | 2-CH3,5-F | CH3 | H/H | yellow resin, 7.03–7.13 (m, 2H) 6.75–6.97 (m, 4H) 5.01 (s, 2H) 3.86 (s, 3H) 2.31 (s, 6H) |
| 1.370 | 5-CH3 | 3-CH2CN | CH3 | CH3/H | |
| 1.371 | 5-CH3 | 3-CH(CH3)CN | CH3 | H/H | |
| 1.372 | 5-CH3 | 3-CHFCN | CH3 | H/H | |
| 1.373 | 5-CH3 | 3-CF2CN | CH3 | H/H | |
| 1.374 | 5-CH3 | 3-CH2C(=S)NH2 | CH3 | H/H | |
| 1.375 | 5-CH3 | 3-CF3 | CH3 | H/H | yellow solid, 7.68 (bs, 1H) 7.53–7.62 (bt, 2H) 7.40–7.47 (t, 1H) 6.92 (s, 1H) 6.75–6.85 (m, 2H) 4.98 (s, 2H) 3.86 (s, 3H) 2.31 (s, 3H) |
| 1.376 | 4-F | 4-OCHF2 | CH3 | H/H | brown crystal, 7.40–7.50 (m, 2H) 7.00–7.10 (m, 3H) 6.58–6.72 (m, 2H) 6.80, 6.50; 6.21 (s, 1H) 4.92 (s, 2H) 3.88 (s, 3H) |
| 1.377 | 4-F | 3,4-di-Cl | CH3 | H/H | light brown crystal, 7.50 (d, 1H) 7.35–7.40(d, 1H) 7.20–7.25 (dd, 2H) 6.98–7.05 (q, 1H) 6.56–6.71 (m, 2H) 4.92 (s, 2H) 3.90 (s, 3H) |
| 1.378 | 4-F | 4-OCH2-phenyl | CH3 | H/H | brown crystal, 7.30–7.45 (m, 7H) 7.00–7.10 (q, 1H) 6.85–6.92 (m, 2H) 6.55–6.70 (m, 2H) 5.05 (s, 2H) 4.91 (s, 2H) 3.88 (s, 3H) |
| 1.379 | 4-F | 4-N-pyrrolyl | CH3 | H/H | light brown crystal, 7.30–7.50 (dq, 4H) 7.08–7.01 (q 2H) 7.0–7.05 (t, 1H) 6.57–6.70 (m, 2H) 6.33 (t, 2H) 4.95 (s, 2H) 3.88 (s, 3H) |
| 1.380 | 4-F | 3,4-di-Cl | CH3 | H/H | yellow crystal, 6.98–7.30 (m, 4H) 6.58–6.70 (m, 2H) 4.90 (s, 2H) 3.89 (s, 3H) |
| 1.381 | 4-Cl | 4-N-pyrrolyl | CH3 | H/H | light brown crystal, 7.30–7.50 (dq, 4H) 7.00–7.10 (m, 3H) 6.88–6.93 (m, 2H) 6.32–6.37 (t, 2H) 4.95 (s, 2H) 3.88 (s, 3H) |
| 1.382 | 4-Cl | 3,4-di-F | CH3 | H/H | yellow crystal, 6.95–7.30 (m, 4H) 6.88–6.94 (m, 2H) 4.92 (s, 2H) 3.88 (s, 3H) |

TABLE 1-continued

| Comp No. | R₁ | R₂ | R | R₃/R₄ | ¹H-NMR (CDCl₃) or M.P./M.S. data |
|---|---|---|---|---|---|
| 1.383 | 4-Br | 3-CH2CN | CH3 | H/H | yellow solid, 7.26–7.42 (m, 4H) 7.00–7.10 (d, 2H) 6.92–6.99 (d, 1H) 4.95 (s, 2H) 3.88 (s, 3H) 3.77 (s, 2H) |
| 1.384 | 4-Br | 4-Cl | CH3 | H/H | light tan solid, 7.24–7.38 (m, 4H) 7.00–7.10 (d, 2H) 6.92–6.99 (d, 1H) 4.95 (s, 2H) 3.88 (s, 3H) |
| 1.385 | 4-Br | 3-Cl | CH3 | H/H | light yellow solid, 7.40 (s, 1H) 7.20–7.35 (m, 3H) 7.00–7.10 (m, 2H) 6.91–6.99 (d, 1H) 4.95 (s, 2H) 3.88 (s, 3H) |
| 1.386 | 4-Br | 4-F | CH3 | H/H | light yellow solid, 7.32–7.46 (m, 2H) 6.94–7.10 (m, 5H) 4.95 (s, 2H) 3.88 (s, 3H) |
| 1.387 | 4-Br | 3-F | CH3 | H/H | white solid, 7.15–7.35 (m, 2H) 6.92–7.14 (m, 5H) 4.95 (s, 2H) 3.88 (s, 3H) |
| 1.388 | 4-Br | 3-Br | CH3 | H/H | light tan solid, 7.55 (s, 1H) 7.43–7.50 (d, 1H) 7.3–7.35 (d, 1H) 7.12–7.20 (t, 1H) 7.00–7.10 (m, 2H) 6.90–6.98 (d, 1H) 4.95 (s, 2H) 3.88 (s, 3H) |
| 1.389 | 4-CH₂C(=O)N(ethyl)₂ | 4-Cl | CH3 | H/H | yellow resin, 7.22–7.40 (m, 4H) 7.05–7.10 (d, 1H) 6.95–7.01 (d, 2H) 5.00 (s, 2H) 3.90 (s, 3H) 3.30–3.70 (bs, 4H) 1.10–1.40 (bs, 4H) |
| 1.390 | 4-CH₂C(=O)N(ethyl)₂ | 3-Cl | CH3 | H/H | yellow resin, 7.40 (s, 1H) 7.20–7.35 (m, 3H) 7.05–7.10 (d, 1H) 6.95–7.01 (d, 2H) 5.00 (s, 2H) 3.90 (s, 3H) 3.30–3.70 (bs, 4H) 1.10–1.40 (bs, 4H) |
| 1.391 | 4-CH₂(=O)N(ethyl)₂ | 3-CH2CN | CH3 | H/H | yellow resin, 7.25–7.42 (m, 4H) 7.05–7.10 (d, 1H) 6.95–7.01 (d, 2H) 5.00 (s, 2H) 3.90 (s, 3H) 3.21 (s, H) 3.30–3.70 (bs, 4H) 1.10–1.40 (bs, 4H) |
| 1.392 | 4-CH₂C(=O)(ethyl)₂ | 3-Br | CH3 | H/H | yellow resin, 7.55 (s, 1H) 7.42–7.48 (d, 1H) 7.31–7.38 (d, 1H) 7.12–7.21 (t, 1H) 7.05–7.10 (d, 1H) 6.95–7.01 (d, 2H) 5.00 (s, 2H) 3.90 (s, 3H) 3.30–3.70 (bs, 4H) 1.10–1.40 (bs, 4H) |
| 1.393 | 4-CH2CO2ethyl | 4-CH2CN | CH3 | H/H | clear yellow oil, 7.25–7.43 (m, 4H) 7.00–7.05 (d, 1H) 6.80–6.90 (m, 2H) 4.95 (s, 2H) 4.10–4.20 (q, 2H) 3.90 (s, 3H) 3.71 (s, 2H) 3.55 (s, 2H) 1.22–2.32 (t, 3H) |
| 1.394 | 4-CH2CO2ethyl | 3-CF3 | CH3 | H/H | brown resin, 7.68 (s, 1H) 7.53–7.60 (bt, 2H) 7.38–7.47 (t, 1H) 7.00–7.05 |

TABLE 1-continued

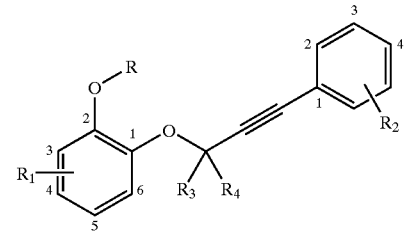

| Comp No. | R₁ | R₂ | R | R₃/R₄ | $^1$H-NMR (CDCl₃) or M.P./M.S. data |
|---|---|---|---|---|---|
| | | | | | (d, 1H) 6.80–6.90 (m, 2H) 4.95 (s, 2H) 4.10–4.20 (q, 2H) 3.90 (s, 3H) 3.55 (s, 2H) 1.22–2.32 (t, 3H) |
| 1.395 | 4-CH2CO2ethyl | 4-Cl | CH3 | H/H | yellow resin, 7.55 (s, 1H) 7.40–7.48 (d, 1H) 7.30–7.38 (d, 1H) 7.12–7.22 (t, 1H) 7.00–7.05 (d, 1H) 6.80–6.90 (m, 2H) 4.95 (s, 2H) 4.10–4.20 (q, 2H) 3.90 (s, 3) 3.57 (s, 2H) 1.22–2.32 (t, 3H) |
| 1.396 | 4-CH2CO2ethyl | 3-Cl | CH3 | H/H | yellow oil, 7.40 (s, 1H) 7.19–7.35 (m, 3H) 7.00–7.05 (d, 1H) 6.80–6.90 (m, 2H) 4.95 (s, 2H) 4.10–4.20 (q, H) 3.90 (s, 3H) 3.57 (s, 2H) 1.22–2.32 (t, 3H) |
| 1.397 | 4-CH2CO2ethyl | 3-Br | CH3 | H/H | yellow resin, 7.55 (s, 1H) 7.40–7.48 (d, 1H) 7.30–7.38 (d, 1H) 7.12–7.22 (t, 1H) 7.00–7.05 (d, 1H) 6.80–6.90 (m, 2H) 4.95 (s, 2H) 4.10–4.20 (q, 2H) 3.90 s, 3H) 3.57 (s, 2H) 1.22–2.32 (t, 3H) |
| 1.398 | 4-CH3 | 4-F | CH3 | H/H | reddish brown crystal, 7.35–7.45 (m, 2H) 6.93–7.05 (m, 3H) 6.7–6.75 (d, 2H) 4.95 (s, 2H) 3.88 (s, 3H) 2.32 (s, 3H) |
| 1.399 | 4-CH3 | 3-F | CH3 | H/H | reddish brown crystal, 6.94–7.35 (m, 5H) 6.70–6.80 (d, 2H) 4.95 (s, 2H) 3.88 (s, 3H) 2.32 (s, 3H) |
| 1.400 | 4-CH3 | 3-CF3 | CH3 | H/H | brown crystal, 7.65–7.68 (bs, 1H) 7.53–7.60 (t, 2H) 7.40–7.45 (t, 1H) 6.96–7.01 (d, 1H) 6.70–6.77 (d, 2H) 4.95 (s, 2H) 3.88 (s, 3H) 2.32 (s, 3H) |
| 1.401 | 4-CF3 | 4-F | CH3 | H/H | yellow solid, 7.33–7.45 (m, 2H) 7.08–7.26 (m, 3H) 6.93–7.05 (t, 2H) 5.02 (s, 2H) 3.94 (s, 3H) |
| 1.402 | 4-CF3 | 3-F | CH3 | H/H | white solid, 7.00–7.33 (m, 7H) 5.02 (s, 2H) 3.94 (s, 3H) |
| 1.403 | 4-CF3 | 3-CF3 | CH3 | H/H | light brown crystal, 7.68–7.70 (bs, 1H) 7.55–7.62 (d, 2H) 7.40–7.48 (t, 1H) 7.21–7.28 (d, 1H) 7.10–7.18 (d, 2H) 5.05 (s, 2H) 3.92 (s, 3H) |
| 1.404 | 4-CF3 | 3-(C=O)2N-piperidinyl, 4-NH2 | CH3 | H/H | |
| 1.405 | H | 3-CH2CH=NOCH3 | CH3 | H/H | |
| 1.406 | H | 3-CH2CH=NOCH3 | CH3 | CH3/H | |
| 1.407 | 4-CH3 | 3-CH2CH=NOCH3 | CH3 | H/H | |
| 1.408 | 4-CH3 | 3-CH2CH=NOCH3 | CH3 | CH3/H | |

TABLE 1-continued

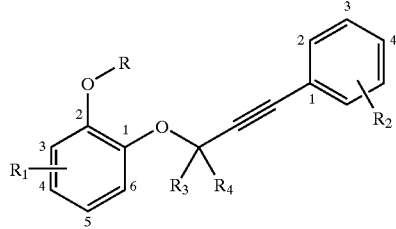

| Comp No. | R₁ | R₂ | R | R₃/R₄ | ¹H-NMR (CDCl₃) or M.P./M.S. data |
|---|---|---|---|---|---|
| 1.409 | 4-F | 3-CH2CH=NOCH3 | CH3 | H/H | |
| 1.410 | 4-F | 3-CH2CH=NOCH3 | CH3 | CH3/H | |
| 1.411 | 4-CN | 3-CH2CH=NOCH3 | CH3 | H/H | |
| 1.412 | 4-CN | 3-CH2CH=NOCH3 | CH3 | CH3/H | |
| 1.413 | 4-CH2CH=NOCH3 | 3-CH2CH=NOCH3 | CH3 | H/H | |
| 1.414 | 4-CH2CH=NOCH3 | 3-CH2CH=NOCH3 | CH3 | CH3/H | |
| 1.415 | 4-CH2CH=CH2 | 3-CH2CH=NOCH3 | CH3 | H/H | |
| 1.416 | 4-CH2CH=CH2 | 3-CH2CH=NOCH3 | CH3 | CH3/H | |
| 1.417 | 4-Cl | 3-CH2CH=NOCH3 | CH3 | CH3/H | |
| 1.418 | 4-Cl | 3-CH2CH=NOCH3 | CH3 | H/H | |
| 1.419 | 4-CF3 | 3-CH2CH=NOCH3 | CH3 | CH3/H | |
| 1.420 | 4-CF3 | 3-CH2CH=NOCH3 | CH3 | H/H | |
| 1.421 | H | 4-CH2CH=NOCH3 | CH3 | H/H | |
| 1.422 | H | 4-CH2CH=NOCH3 | CH3 | H/H | |
| 1.423 | 4-F | 2-CH2CH=NOCH3 | CH3 | H/H | |
| 1.424 | 4-F | 2-CH2CH=NOCH3 | CH3 | H/H | |
| 1.425 | H | 3-CH2C(=S)NH2 | CH3 | H/H | |
| 1.426 | H | 3-CH2C(=S)NH2 | CH3 | CH3/H | |
| 1.427 | 4-CH3 | 3-CH2C(=S)NH2 | CH3 | H/H | |
| 1.428 | 4-CH3 | 3-CH2C(=S)NH2 | CH3 | CH3/H | |
| 1.429 | 4-F | 3-CH2C(=S)NH2 | CH3 | H/H | |
| 1.430 | 4-F | 3-CH2C(=S)NH2 | CH3 | CH3/H | |
| 1.431 | 4-CN | 3-CH2C(=S)NH2 | CH3 | H/H | |
| 1.432 | 4-CN | 3-CH2C(=S)NH2 | CH3 | CH3/H | |
| 1.433 | 4-CH2CH=NOCH3 | 3-CH2C(=S)NH2 | CH3 | H/H | |
| 1.434 | 4-CH2CH=NOCH3 | 3-CH2C(=S)NH2 | CH3 | CH3/H | |
| 1.435 | 4-CH2CH=CH2 | 3-CH2C(=S)NH2 | CH3 | H/H | |
| 1.436 | 4-CH2CH=CH2 | 3-CH2C(=S)NH2 | CH3 | CH3/H | |
| 1.437 | 4-Cl | 3-CH2C(=S)NH2 | CH3 | CH3/H | |
| 1.438 | 4-Cl | 3-CH2C(=S)NH2 | CH3 | H/H | |
| 1.439 | 4-CF3 | 3-CH2C(=S)NH2 | CH3 | CH3/H | |
| 1.440 | 4-CF3 | 3-CH2C(=S)NH2 | CH3 | H/H | |
| 1.441 | H | 4-CH2C(=S)NH2 | CH3 | H/H | |
| 1.442 | H | 4-CH2C(=S)NH2 | CH3 | H/H | |
| 1.443 | 4-F | 2-CH2C(=S)NH2 | CH3 | H/H | |
| 1.444 | 4-F | 2-CH2C(=S)NH2 | CH3 | H/H | |
| 1.445 | 4-CH2CN, 6-OCH3 | 4-OCF3 | CH3 | H/H | MS 392 (99) |
| 1.446 | H | 3-Cl | CH3 | H/H | |
| 1.447 | H | 4-CH2CN | CH₃ | H/H | MS 277 (99) |
| 1.448 | 4-CH2CN | 2-CH3, 4-NO2 | CH3 | H/H | |
| 1.449 | 3-F | 3-C(CH3)2CN | CH3 | H/H | |
| 1.450 | 3-F | 3-CH2CN | CH3 | H/H | |
| 1.451 | 3-F | 4-Cl | CH3 | H/H | |
| 1.452 | 3-F | 3-Cl | CH3 | H/H | 7.15–7.40 (m, 4H) 7.38–7.45 (dd, 1H) 6.15–6.92 (m, 2H) 4.85 (s, 2H) 3.88 (s, 3H) |
| 1.453 | 3-F | 3-Br | CH3 | H/H | 7.15–7.55 (m, 4H) 6.15–6.92 (m, 3H) 4.85 (s, 2H) 3.88 (s, 3H) |
| 1.454 | 3-F | 3,4,5-tri-OCH3 | CH3 | CH3/H | |
| 1.455 | 3-F | 3-CN, 4-F | CH3 | H/H | |
| 1.456 | 3-F | 3-CN | CH3 | H/H | |
| 1.457 | 3-F | 3-CH2CN | CH3 | CH3/H | |
| 1.458 | 5-F | 3-C(CH3)2CN | CH3 | H/H | |
| 1.459 | 5-F | 3-CH2CN | CH3 | H/H | yellow resin, 7.22–7.40 (d, 2H) 6.75–6.90 (dd, 2H) 6.60–6.70 (m, 2H) 6.61–6.72 (dt, 1H) 4.96 (s, 2H) 3.80 (s, 3H) 3.65 (s, 2H) |
| 1.460 | 5-F | 4-Cl | CH3 | H/H | brown resin, 7.22–7.30 (dd, 2H), 7.30–7.40 (dd, |

TABLE 1-continued

| Comp No. | R₁ | R₂ | R | R₃/R₄ | ¹H-NMR (CDCl₃) or M.P./M.S. data |
|---|---|---|---|---|---|
| | | | | | 2H) 6.80–6.90 (m, 2H), 6.61–6.72 (dt, 1H), 4.96 (s, 2H) 3.86 (s, 3H) |
| 1.461 | 5-F | 3-Cl | CH3 | H/H | yellow resin, 7.41 (s, 1H) 7.20–7.34 (m, 3H) 6.78–6.91 (m, 2H) 6.61–6.72 (dt, 1H) 4.96 (s, 2H) 3.86 (s, 3H) |
| 1.462 | 5-F | 3-Br | CH3 | H/H | brown resin, 7.58 (s, 1H) 7.42–7.50 (d, 1H) 7.30–7.38 (d, 1H) 7.11–7.20 (t, 1H) 6.80–6.90 (m, 2H) 6.61–6.72 (dt, 1H) 4.96 (s, 2H) 3.86 (s, 3H) |
| 1.463 | 5-F | 3,4,5-tri-OCH3 | CH3 | CH3/H | |
| 1.464 | 5-F | 3-CN, 4-F | CH3 | H/H | |
| 1.465 | 5-F | 3-CN | CH3 | H/H | |
| 1.466 | 5-F | 3-CH2CN | CH3 | CH3/H | |
| 1.467 | 4,5-di-F | 3-C(CH3)2CN | CH3 | H/H | |
| 1.468 | 4,5-di-F | 3-CH2CN | CH3 | H/H | |
| 1.469 | 4,5-di-F | 4-Cl | CH3 | H/H | |
| 1.470 | 4,5-di-F | 3-Cl | CH3 | H/H | |
| 1.471 | 4,5-di-F | 3-Br | CH3 | H/H | |
| 1.472 | 4,5-diF | 3,4,5-tri-OCH3 | CH3 | CH3/H | |
| 1.473 | 4,5-di-F | 3-CN, 4-F | CH3 | H/H | |
| 1.474 | 4,5-di-F | 3-CN | CH3 | H/H | |
| 1.475 | 4,5-di-F | 3-CH2CN | CH3 | CH3/H | |
| 1.476 | 3,5-di-F | 3-C(CH3)2CN | CH3 | H/H | |
| 1.477 | 3,5-di-F | 3-CH2CN | CH3 | H/H | |
| 1.478 | 3,5-di-F | 4-Cl | CH3 | H/H | |
| 1.479 | 3,5-di-F | 3-Cl | CH3 | H/H | |
| 1.480 | 3,5-di-F | 3-Br | CH3 | H/H | |
| 1.481 | 3,5-di-F | 3,4,5-tri-OCH3 | CH3 | CH3/H | |
| 1.482 | 3,5-di-F | 3-CN, 4-F | CH3 | H/H | |
| 1.483 | 3,5-di-F | 3-CN | CH3 | H/H | |
| 1.484 | 3,5-di-F | 3-CH2CN | CH3 | CH3/H | |
| 1.485 | 3,4-di-F | 3-C(CH3)2CN | CH3 | H/H | |
| 1.486 | 3,4-di-F | 3-CH2CN | CH3 | H/H | |
| 1.487 | 3,4-di-F | 4-Cl | CH3 | H/H | 7.15–7.34 (m, 4H), 6.85–7.04 (dd, 1H), 6.65–6.75 (dd, 1H) 4.85 (s, 2H) 3.88 (s, 3H) |
| 1.488 | 3,4-diF | 3-Cl | CH3 | H/H | 7.15–7.34 (m, 4H), 6.85–7.04 (dd, 1H) 6.65–6.75 (dd, 1H) 4.90 (s, 2H) 3.85 (s, 3H) |
| 1.489 | 3,4-di-F | 3-Br | CH3 | H/H | 7.15–7.54 (m, 4H), 6.85–7.04 (dd, 1H) 6.65–6.75 (dd, 1H) 4.90 (s, 2H) 3.88 (s, 3H) |
| 1.490 | 3,4-di-F | 3,4,5-tri-OCH3 | CH3 | CH3/H | |
| 1.491 | 3,4-di-F | 3-CN, 4-F | CH3 | H/H | |
| 1.492 | 3,4-di-F | 3-CN | CH3 | H/H | |
| 1.493 | 3,4-di-F | 3-CH2CN | CH3 | CH3/H | |
| 1.494 | 5,6-di-F | 4-Cl | CH3 | H/H | |
| 1.495 | 5,6-di-F | 3-Cl | CH3 | H/H | |
| 1.496 | 5,6-di-F | 3-Br | CH3 | H/H | |
| 1.497 | 5,6-di-F | 3-C(CH3)2CN | CH3 | CH3/H | |
| 1.498 | 5,6-di-F | 3-CN, 4-F | CH3 | H/H | |
| 1.499 | 5,6-di-F | 3-CN | CH3 | H/H | |
| 1.500 | 5,6-di-F | 3-CH2CN | CH3 | CH3/H | |
| 1.501 | 4-CN | 4-CH3 | CH3 | H/H | oil |

TABLE 1-continued

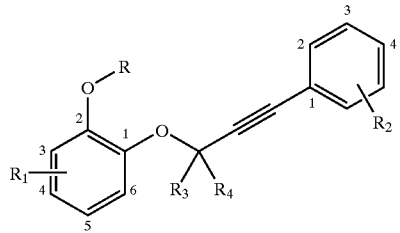

| Comp No. | $R_1$ | $R_2$ | R | $R_3/R_4$ | $^1$H-NMR (CDCl$_3$) or M.P./M.S. data |
|---|---|---|---|---|---|
| 1.502 | 4-CN | 3-NH2 | CH3 | H/H | oil |
| 1.503 | 4-CN | 3-CO2ethyl | CH3 | H/H | oil |
| 1.504 | 4-CN | H | CH3 | H/H | oil |
| 1.505 | 4-CN | 3-NO2 | CH3 | H/H | oil |
| 1.506 | 4-CN | 2-F | CH3 | H/H | oil |
| 1.507 | 4-CN | 3-ethyl | CH3 | H/H | |
| 1.508 | 4-CN | 3-F | CH3 | H/H | oil |
| 1.509 | 4-CN | 4-OCH3 | CH3 | H/H | oil |
| 1.510 | 4-CN | 2,3-di-Cl | CH3 | H/H | oil |
| 1.511 | 4-CN | 4-F | CH3 | H/H | oil |
| 1.512 | 4-CN | 2-Cl | CH3 | H/H | oil |
| 1.513 | 4-CN | 3,4-di-CH3 | CH3 | H/H | oil |
| 1.514 | 4-CN | 2,4-di-Cl | CH3 | H/H | oil |
| 1.515 | 4-CN | 2,3-di-CH3 | CH3 | H/H | oil |
| 1.516 | 4-F | 3-CO2ethyl | CH3 | H/H | oil |
| 1.517 | 4-F | 2-CO2CH3 | CH3 | H/H | oil |
| 1.518 | 4-F | 3-ethyl | CH3 | H/H | |
| 1.519 | 4-F | H | CH3 | H/H | oil |
| 1.520 | 4-F | 3-NO2 | CH3 | H/H | oil |
| 1.521 | 4-F | 3-t-butyl | CH3 | H/H | |
| 1.522 | 4-F | 3,5-di-(CH$_2$CN) | CH3 | H/H | |
| 1.523 | 4-F | 3,5-di-(CH$_2$CN) | CH3 | CH3/H | |
| 1.524 | 4-F | 4-OCH3 | CH3 | H/H | oil |
| 1.525 | 4-F | 2,3-di-Cl | CH3 | H/H | oil |
| 1.526 | 4-F | 3-i-propyl | CH3 | H/H | |
| 1.527 | 4-F | 2-Cl | CH3 | H/H | oil |
| 1.528 | 4-F | 3,4-di-CH3 | CH3 | H/H | oil |
| 1.529 | 4-F | 2,4-di-F | CH3 | H/H | oil |
| 1.530 | 4-F | 4-CO2ethyl | CH3 | H/H | oil |
| 1.531 | 4-F | 4-CO2CH3 | CH3 | H/H | oil |
| 1.532 | 4-Cl | 3-CO2ethyl | CH3 | H/H | oil |
| 1.533 | 4-Cl | 2-OCH3, 5-NO2 | CH3 | H/H | oil |
| 1.534 | 4-Cl | 3,5-di-(CH$_2$CN) | CH3 | H/H | |
| 1.535 | 4-Cl | H | CH3 | H/H | oil |
| 1.536 | 4-Cl | 3-NO2 | CH3 | H/H | oil |
| 1.537 | 4-Cl | 2-F | CH3 | H/H | oil |
| 1.538 | 4-Cl | 3,5-di-(CH$_2$CN) | CH3 | CH$_3$/H | |
| 1.539 | 4-Cl | 3-ethyl | CH3 | H/H | |
| 1.540 | 4-Cl | 3-t-butyl | CH3 | H/H | |
| 1.541 | 4-Cl | 2,3-di-Cl | CH3 | H/H | oil |
| 1.542 | 4-Cl | 3-i-propyl | CH3 | H/H | |
| 1.543 | 4-Cl | 3,4-di-CH3 | CH3 | H/H | |
| 1.544 | 4-Cl | 2,4-di-Cl | CH3 | H/H | oil |
| 1.545 | 4-Cl | 2,3-di-CH3 | CH3 | H/H | oil |
| 1.546 | 4-Cl | 4-CO2ethyl | CH3 | H/H | oil |
| 1.547 | 4-Cl | 4-CO2CH3 | CH3 | H/H | oil |
| 1.548 | 4-Cl | 3-OCH2CN | CH3 | H/H | |
| 1.549 | 4-CN | 3-OCH3 | CH3 | H/H | oil |
| 1.550 | 4-CN | 3-OCH2CN | CH3 | H/H | |
| 1.551 | 4-CN | 2-F, 4-Br | CH3 | H/H | oil |
| 1.552 | 4-F | 4-CH3 | CH3 | H/H | oil |
| 1.553 | 4-F | 3-OCH2CN | CH3 | H/H | |
| 1.554 | 4-F | 2,4-di-Cl | CH3 | H/H | oil |
| 1.555 | 4-F | 2-Cl, 3-CF3 | CH3 | H/H | oil |
| 1.556 | 4-Cl | 4-CH3 | CH3 | H/H | oil |
| 1.557 | 4-Cl | 2-CO2CH3 | CH3 | H/H | oil |
| 1.558 | 4-Cl | 4-OCH3 | CH3 | H/H | oil |
| 1.559 | 4-Cl | 3-CH2CN | CH3 | CH$_3$/H | |
| 1.560 | 4-Cl | 3-CH2CN | CF3 | H/H | |
| 1.561 | 4-CN | 3,5-di-CH3 | CH3 | H/H | oil |
| 1.562 | 4-CN | 3,4-di-Cl | CH3 | H/H | oil |
| 1.563 | 4-CN | 3-F, 4-CH3 | CH3 | H/H | oil |
| 1.564 | 4-CN | 2-Cl, 4-F | CH3 | H/H | oil |

TABLE 1-continued

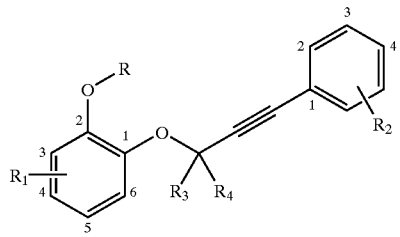

| Comp No. | R₁ | R₂ | R | R₃/R₄ | ¹H-NMR (CDCl₃) or M.P./M.S. data |
|---|---|---|---|---|---|
| 1.565 | 4-CN | 3-Cl, 4-F | CF3 | H/H | oil |
| 1.566 | 4-CN | 2-CH3, 3-Cl | CF3 | H/H | oil |
| 1.567 | 4-CN | 2-CH3, 5-F | CH3 | H/H | oil |
| 1.568 | 4-Cl | 3-Cl, 4-CH3 | CH3 | H/H | oil |
| 1.569 | 4-CN | 2-F, 4-Cl | CH3 | H/H | oil |
| 1.570 | 4-CN | 2-CH3, 4-Cl | CH3 | H/H | oil |
| 1.571 | 4-CN | 2-ethyl, 4-Br | CH3 | H/H | oil |
| 1.572 | 4-CN | 2-OCH3, 5-Cl | CH3 | H/H | oil |
| 1.573 | 4-CN | 2-OCF3, 4-Br | CH3 | H/H | oil |
| 1.574 | 4-F | 3,5-di-CH3 | CH3 | H/H | oil |
| 1.575 | 4-F | 3,5-di-OCF3 | CH3 | H/H | oil |
| 1.576 | 4-F | 3-CH2CN | —SO2CH3 | CH₃/H | |
| 1.577 | 4-F | 3,5-di-Cl | CH3 | H/H | oil |
| 1.578 | 4-F | 3-F, 4-CH3 | CH3 | H/H | oil |
| 1.579 | 4-F | 3-Cl, 4-F | CH3 | CH₃/H | oil |
| 1.580 | 4-F | 2-CH3, 3-Cl | CH3 | H/H | oil |
| 1.581 | 4-F | 2-CH3, 5-F | CH3 | H/H | oil |
| 1.582 | 4-F | 3-Cl, 4-CH3 | CH3 | H/H | oil |
| 1.583 | 4-F | 4-CN | CH3 | H/H | |
| 1.584 | 4-F | 2-CH3, 4-Cl | CH3 | H/H | oil |
| 1.585 | 4-F | 2-OCH3, 5-Cl | CH3 | H/H | oil |
| 1.586 | 4-F | 2-OCF3, 4-Br | CH3 | H/H | oil |
| 1.587 | 4-Cl | 2,5-di-Cl | CH3 | H/H | oil |
| 1.588 | 4-Cl | 3,5-di-Cl | CH3 | H/H | oil |
| 1.589 | 4-Cl | 3,5-di-OCF3 | CH3 | H/H | oil |
| 1.590 | 4-Cl | 3-CH2CN | —CN | H/H | |
| 1.591 | 4-Cl | 3-F, 4-CH3 | CH3 | H/H | oil |
| 1.592 | 4-Cl | 2-Cl, 4-F | CH3 | H/H | oil |
| 1.593 | 4-Cl | 2-Cl, 6-CH3 | CH3 | H/H | oil |
| 1.594 | 4-Cl | 3-Cl, 4-F | CH3 | H/H | oil |
| 1.595 | 4-Cl | 2-CH3, 3-Cl | CH3 | H/H | oil |
| 1.596 | 4-Cl | 2-CH3, 5-F | CH3 | H/H | oil |
| 1.597 | 4-Cl | 3-Cl, 4-CH3 | CH3 | H/H | oil |
| 1.598 | 4-Cl | 2-CH3, 4-F | CH3 | H/H | oil |
| 1.599 | 4-Cl | 2-F, 4-Cl | CH3 | H/H | oil |
| 1.600 | 4-Cl | 2-CH3, 4-Cl | CH3 | H/H | oil |
| 1.601 | 4-Cl | 2-ethyl, 4-Br | CH3 | H/H | oil |
| 1.602 | 4-Cl | 2-OCH3, 5-Cl | CH3 | H/H | oil |
| 1.603 | 4-Cl | 2-OCF3, 4-Br | CH3 | H/H | oil |
| 1.604 | 4-CN | 3-CH2CN | —CN | H/H | |
| 1.605 | 4-CN | 3-CH3, 4-F | CH3 | H/H | oil |
| 1.606 | 4-CN | 2-Cl, 4-Br | CH3 | H/H | oil |
| 1.607 | 4-Cl | 3,5-di-Cl | CH3 | H/H | oil |
| 1.608 | 4-Cl | 2-Cl, 4-Br | CH3 | H/H | oil |
| 1.609 | 4-CHF2 | 3-CH2CN | CH3 | H/H | |
| 1.610 | 4-ethyl | 3-CH2CN | CH3 | H/H | |
| 1.611 | 4-ethyl | 3-CH2CN | CH3 | CH₃/H | |
| 1.612 | 3,6-di-F | 3-C(CH3)2CN | CH3 | H/H | |
| 1.613 | 3,6-di-F | 3-CH2CN | CH3 | H/H | |
| 1.614 | 3,6-di-F | 4-Cl | CH3 | H/H | |
| 1.615 | 3,6-di-F | 3-Cl | CH3 | H/H | |
| 1.616 | 3,6-di-F | 3-Br | CH3 | H/H | |
| 1.617 | 3,6-di-F | 3,4,5-tri-OCH3 | CH3 | CH₃/H | |
| 1.618 | 3,6-di-F | 3-CN, 4-F | CH3 | H/H | |
| 1.619 | 3,6-di-F | 3-CN | CH3 | H/H | |
| 1.620 | 3,6-di-F | 3-CH2CN | CH3 | CH₃/H | |
| 1.621 | 4-ethenyl | 3-CH2CN | CH3 | H/H | |
| 1.622 | 4-ethynyl | 3-CH2CN | CH3 | H/H | |
| 1.623 | 4-allyl | 3-CH2CN | CH3 | H/H | |
| 1.624 | 4-F | 3-CH2CN | CH3 | OCH₃/H | |
| 1.625 | H | 3-CH2CN | CH3 | OCH₃/H | |
| 1.626 | 4-CN | 3-CH2CN | CH3 | OCH₃/H | |
| 1.627 | 4-Cl | 3-CH2CN | CH3 | OCH₃/H | |

TABLE 1-continued

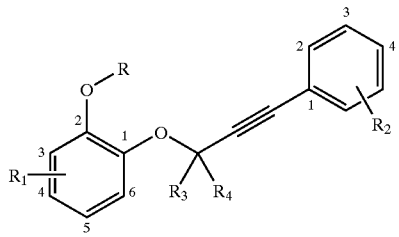

| Comp No. | $R_1$ | $R_2$ | R | $R_3/R_4$ | $^1$H-NMR (CDCl$_3$) or M.P./M.S. data |
|---|---|---|---|---|---|
| 1.628 | 4-CH3 | 3-CH2CN | CH3 | OCH$_3$/H | |
| 1.629 | 4-CH2CN | 3-CH2CN | CH3 | OCH$_3$/H | |
| 1.630 | 4-CF3 | 3-CH2CN | CH3 | OCH$_3$/H | |
| 1.631 | 4-Br | 3-CH2CN | CH3 | OCH$_3$/H | |
| 1.632 | 4-OCH3 | 3-CH2CN | CH3 | OCH$_3$/H | |
| 1.633 | 4-SO2CH3 | 3-CH2CN | CH3 | OCH$_3$/H | |
| 1.634 | 4-OSO2CH3 | 3-CH2CN | CH3 | OCH$_3$/H | |
| 1.635 | 4-CH=NOCH3 | 3-CH2CN | CH3 | OCH$_3$/H | |
| 1.636 | 4-CH=NOethyl | 3-CH2CN | CH3 | OCH$_3$/H | |
| 1.637 | 4-OCF3 | 3-CH2CN | CH3 | OCH$_3$/H | |
| 1.638 | 4-ethyl | 3-CH2CN | CH3 | OCH$_3$/H | |
| 1.639 | 4-ethenyl | 3-CH2CN | CH3 | OCH$_3$/H | |
| 1.640 | 4-ethynyl | 3-CH2CN | CH3 | OCH$_3$/H | |
| 1.641 | 4-Cl | 3-CH2CN | CH3 | F/F | |
| 1.642 | 4-CH3 | 3-CH2CN | CH3 | F/F | |
| 1.643 | 4-CN | 3-CH2CN | CH3 | F/F | |
| 1.644 | 4-F | 3-CH2CN | CH3 | F/F | |
| 1.645 | 4-Br | 3-CH2CN | CH3 | F/F | |
| 1.646 | 4-CF3 | 3-CH2CN | CH3 | F/F | |
| 1.647 | 4-CHF2 | 3-CH2CN | CH3 | F/F | |
| 1.648 | H | 3-CH2CN | CH3 | F/F | |
| 1.649 | 4-CH2CN | 3-CH2CN | CH3 | F/F | |
| 1.650 | 3,6-di-F | 3-CH2CN | CH3 | F/F | |

BOLOGICAL EXAMPLES

Eample B1

Pre-emergence Herbicidal Action

Monocot and dicot test plants are sown in standard soil in plastic pots. Immediately after sowing, the test substances are sprayed on as an aqueous suspension [prepared from a wettable powder (Example F3, b) of WO 97/34485] or as an emulsion [prepared from an emulsion concentrate (Example F1 c) of WO 97/34485] in an optimal dosage (500 l of water/ha). The test plants are then cultivated in the greenhouse under optimum conditions.

The test is evaluated 4 weeks later on a rating scale of 1–9 (1=total damage, 9=no action). Ratings of 1 to 4 (especially 1 to 3) denote good to very good herbicidal action.

Example B2

Post-emergence Herbicidal Action

Monocot and dicot test plants are sown in standard soil in plastic pots. At the 2- to 3-leaf stage, the test plants are sprayed with test substances as an aqueous suspension [prepared from a wettable powder (Example F3, b) of WO 97/34485] or as an emulsion [prepared from an emulsion concentrate (Example F1 c) of WO 97/34485] in an optimal dosage (500 l of water/ha). The test plants are then cultivated in the greenhouse under optimum conditions.

The test is evaluated 2 to 3 weeks later on a rating scale of 1–9 (1=total damage, 9=no action). Ratings of 1 to 4 (especially 1 to 3) denote good to very good herbicidal action.

Table biology 1: Preemergence test at 1 kg/ha:

| Compound | Setaria | Panicum | Digitaria | Amaranthus | Chenopodium | Stellaria | Veronica |
|---|---|---|---|---|---|---|---|
| 1.104 | 4 | 7 | 7 | 1 | 1 | 1 | 1 |
| 1.098 | 1 | 1 | 3 | 1 | 1 | 1 | 1 |
| 1.198 | 3 | 1 | 1 | 1 | 1 | 1 | 1 |
| 1.109 | 6 | 1 | 1 | 1 | 1 | 1 | 1 |
| 1.168 | 4 | 1 | 3 | 1 | 2 | 1 | 4 |
| 1.033 | 2 | 2 | 1 | 1 | 1 | 1 | 1 |

Table biology 2: Postemergence test at 1 kg/ha:

| Entry | Amaranthus | Chenopodium | Stellaria |
|---|---|---|---|
| 1.104 | 2 | 2 | 3 |
| 1.098 | 1 | 1 | 2 |
| 1.198 | 1 | 1 | 3 |
| 1.109 | 1 | 4 | 2 |
| 1.095 | 1 | 2 | 2 |
| 1.033 | 4 | 2 | 2 |

Similar results are obtained by formulating the compounds of formula I in accordance with the other examples of WO 97/34485.

Similar results are obtained by formulating the compounds of formula I in accordance with the other examples of WO 97/34485.

What is claimed is:

1. A compound of the formula I

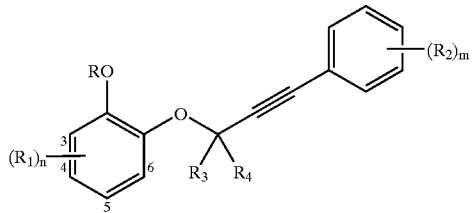

wherein

R is H, —$COR_{12}$, $C_{1-8}$alkyl optionally substituted by one or more substituents selected from halogen, $C_{1-4}$alkoxy and phenyl optionally substituted by one or more substituents selected from halogen, $C_{1-4}$alkyl, halo-$C_{1-4}$alkyl, and $C_{1-4}$alkoxy, $C_{3-8}$alkenyl optionally substituted by one or more substituents selected from halogen, $C_{1-4}$alkoxy and phenyl optionally substituted by one or more substituents selected from halogen, $C_{1-4}$alkyl, halo-$C_{1-4}$alkyl, and $C_{1-4}$alkoxy, $C_{3-8}$alkinyl optionally substituted by one or more substituents selected from halogen, $C_{1-4}$alkoxy and phenyl optionally substituted by one or more substituents selected from halogen, $C_{1-4}$alkyl, halo-$C_{1-4}$alkyl, and $C_{1-4}$alkoxy, $C_{3-6}$cycloalkyl optionally substituted by one or more substituents selected from halogen, $C_{1-4}$alkoxy, and phenyl optionally substituted by one or more substituents selected from halogen, $C_{1-4}$alkyl, halo-$C_{1-4}$alkyl, and $C_{1-4}$alkoxy, or phenyl optionally substituted by one or more substituents selected from halogen, —$CH_3$, —$CF_3$, and —$OCH_3$;

$R_1$ is halogen, —$CO_2R_7$, —$COR_{12}$, —$XR_{13}$, $C_{1-8}$-alkyl optionally substituted by one or more substituents selected from halogen, —$CO_2R_7$, —$COR_{12}$, and $C_{3-6}$cycloalkyl, $C_{2-8}$alkenyl optionally substituted by one or more substituents selected from halogen, —$CO_2R_7$, —$COR_{12}$, and $C_{3-6}$cycloalkyl or $C_{2-8}$alkinyl optionally substituted by one or more substituents selected from halogen, —$CO_2R_7$, —$COR_{12}$, and $C_{3-6}$cycloalkyl, $C_{3-6}$cycloalkyl optionally substituted by one or more substituents selected from halogen, —$CO_2R_7$, and —$COR_{12}$, or phenyl optionally substituted by one or more substituents selected from halogen, $C_{1-4}$alkyl, halo-$C_{1-4}$alkyl, and $C_{1-4}$alkoxy;

$R_2$ is —CN, $C_{1-8}$-alkyl substituted by one or more —CN, $C_{2-8}$alkenyl substituted by one or more —CN, $C_{2-8}$alkinyl substituted by one or more —CN, or $C_{3-6}$cycloalkyl substituted by one or more —CN;

$R_7$ is H, $C_{1-8}$alkyl optionally substituted by one or more substituents selected from halogen and $C_{1-4}$alkoxy, $C_{3-8}$alkenyl optionally substituted by one or more halogen, $C_{3-8}$alkinyl optionally substituted by one or more halogen or phenyl optionally substituted by one or more substituents selected from halogen, $C_{1-4}$alkyl, halo-$C_{1-4}$alkyl, and $C_{1-4}$alkoxy;

$R_{12}$ is H, $C_{1-4}$alkyl, halo-$C_{1-4}$alkyl or $C_{3-6}$cycloalkyl;

$R_{13}$ is $C_{1-8}$alkyl optionally substituted by one or more substituents selected from halogen and $C_{1-4}$alkoxy, $C_{3-8}$alkenyl, $C_{3-8}$alkinyl and H;

X is —O—;

$R_3$ or $R_4$ are independent of one another H, halogen, $C_{1-4}$alkyl or $C_{1-4}$alkoxy;

n is a number 0, 1, 2, 3 or 4; and m is a number 0, 1, 2, 3, 4 or 5; and the sum of n and m is equal or greater than 1.

2. A compound of formula I according to claim 1, wherein R is H, $C_{1-8}$alkyl optionally substituted by one or more halogen; and $R_1$ is halogen, —$XR_{13}$, $C_{1-8}$-alkyl or $C_{3-8}$alkenyl.

3. A compound of formula I according to claim 1, wherein $R_2$ is —CN, or $C_{1-8}$-alkyl substituted by one or more —CN and $R_7$ is H or $C_{1-8}$alkyl.

4. A compound of formula I according to claim 1, wherein R is H or $C_{1-8}$alkyl optionally substituted by one or more halogen; $R_1$ is halogen, —$XR_{13}$, $C_{1-8}$-alkyl; or $C_{3-8}$alkenyl; $R_2$ is —CN or $C_{1-8}$-alkyl substituted by one or more —CN; $R_7$ is H or $C_{1-8}$alkyl; $R_3$ or $R_4$ are independent of one another H or $C_{1-4}$alkyl; n is a number 0, 1 or 2; and m is number 0, 1, 2, 3 or 4; and the sum of n and m is equal or greater 1.

5. A compound of formula I according to claim 1, wherein $R_2$ is —CN.

6. A compound of formula I according to claim 1, wherein $R_2$ is $C_{1-8}$alkyl substituted by —CN.

7. A compound of formula I according to claim 1, wherein R is $CH_3$.

8. A method for the preparation of a compound of formula I according to claim 1, which comprises an alkylation of a substituted phenol by treatment with a base and a propargylic derivative under the conditions used for etherification of phenols, followed by coupling the propargylic ether with an activated benzene using typical conditions for the Sonogashira reaction.

9. A herbicidal and plant growth inhibiting composition, which comprises a herbicidally effective amount of the compound of formula I according to claim 1 and an inert carrier.

10. A method of controlling undesirable plant growth, which comprises treating the plants or the locus thereof with a herbicidally effective amount of a compound of formula I according to claim 1 or of a composition containing such a compound.

11. A method of inhibiting undesirable plant growth, which comprises treating the plants or the locus thereof with a herbicidally effective amount of compound of formula I according to claim 1 or of a composition containing such a compound.

* * * * *